US012708415B2

(12) United States Patent
Mauldin et al.

(10) Patent No.: US 12,708,415 B2
(45) **Date of Patent: *Aug. 18, 2026**

(54) FENESTRATED IMPLANT

(71) Applicant: SI-Bone Inc., Santa Clara, CA (US)

(72) Inventors: Richard G. Mauldin, Erie, CO (US); Scott A. Yerby, Montara, CA (US); Mark A. Reiley, Delray Beach, CA (US); Bret W. Schneider, San Jose, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,547

(22) Filed: Jun. 4, 2024

(65) Prior Publication Data

US 2024/0398453 A1 Dec. 5, 2024

Related U.S. Application Data

(63) Continuation of application No. 17/822,360, filed on Aug. 25, 2022, now Pat. No. 12,023,079, which is a (Continued)

(51) Int. Cl.
*A61B 17/84* (2006.01)
*A61B 17/68* (2006.01)

(Continued)

(52) U.S. Cl.
CPC .............. *A61B 17/84* (2013.01); *A61B 17/68* (2013.01); *A61B 17/7055* (2013.01); *A61B 17/1604* (2013.01); *A61B 17/1664* (2013.01); *A61B 17/1671* (2013.01); *A61B 17/1697* (2013.01); *A61B 17/1757* (2013.01); *A61B 17/8897* (2013.01); *A61F 2002/30995* (2013.01)

(58) Field of Classification Search
CPC ... A61B 17/72; A61B 17/744; A61B 17/7208; A61B 17/7283; A61B 17/846; A61B 17/848; A61B 17/7098
See application file for complete search history.

(56) References Cited

U.S. PATENT DOCUMENTS 1,951,278 A 3/1934 Ericsson
2,136,471 A 11/1938 Schneider (Continued)

FOREIGN PATENT DOCUMENTS

CN 1128944 A 8/1996
CN 1190882 A 8/1998

(Continued)

OTHER PUBLICATIONS

Acumed; Acutrak Headless Compressioin Screw (product information); 12 pgs; @2005; retrieved Sep. 25, 2014 from http://www.rcsed.ac.uk/fellows/Ivanrensburg/classification/surgtech/acumed/manuals/acutrak-brochure%200311.pdf.

(Continued)

*Primary Examiner* — Anu Ramana
(74) *Attorney, Agent, or Firm* — Shay Glenn LLP

(57) ABSTRACT

The present invention relates generally to implants used in medical procedures such as bone fixation or fusion. More specifically, this application relates to fenestrated implants used in bone fixation or fusion.

8 Claims, 33 Drawing Sheets

Related U.S. Application Data continuation of application No. 17/649,544, filed on Jan. 31, 2022, now Pat. No. 11,446,069, which is a continuation of application No. 16/552,912, filed on Aug. 27, 2019, now Pat. No. 11,291,485, which is a continuation of application No. 13/888,249, filed on May 6, 2013, now Pat. No. 10,426,533.

(60) Provisional application No. 61/642,681, filed on May 4, 2012.

(51) Int. Cl.

*A61B 17/70* (2006.01)
*A61B 17/16* (2006.01)
*A61B 17/17* (2006.01)
*A61B 17/88* (2006.01)
*A61F 2/30* (2006.01)

(56) References Cited

U.S. PATENT DOCUMENTS 2,243,717 A 5/1941 Moreira
2,414,882 A 1/1947 Longfellow
2,562,419 A 7/1951 Ferris
2,675,801 A 4/1954 Bambara et al.
2,697,433 A 12/1954 Zehnder
3,076,453 A 2/1963 Tronzo
3,506,982 A 4/1970 Steffee
3,694,821 A 10/1972 Moritz
3,709,218 A 1/1973 Halloran
3,744,488 A 7/1973 Cox
4,059,115 A 11/1977 Jumashev et al.
4,156,943 A 6/1979 Collier
4,197,645 A 4/1980 Scheicher
4,292,964 A 10/1981 Ulrich
4,341,206 A 7/1982 Perrett et al.
4,344,190 A 8/1982 Lee et al.
4,399,813 A 8/1983 Barber
4,423,721 A 1/1984 Otte et al.
4,475,545 A 10/1984 Ender
4,501,269 A 2/1985 Bagby
4,569,338 A 2/1986 Edwards
4,612,918 A 9/1986 Slocum
4,622,959 A 11/1986 Marcus
4,630,601 A 12/1986 Harder et al.
4,638,799 A 1/1987 Moore
4,657,550 A 4/1987 Daher
4,743,256 A 5/1988 Brantigan
4,773,402 A 9/1988 Asher et al.
4,787,378 A 11/1988 Sodhi
4,790,303 A 12/1988 Steffee
4,834,757 A 5/1989 Brantigan
4,846,162 A 7/1989 Moehring
4,877,019 A 10/1989 Vives
4,878,915 A 11/1989 Brantigan
4,898,186 A 2/1990 Ikada et al.
4,904,261 A 2/1990 Dove et al.
4,950,270 A 8/1990 Bowman et al.
4,961,740 A 10/1990 Ray et al.
4,969,888 A 11/1990 Scholten et al.
4,981,481 A 1/1991 Kranz et al.
5,034,011 A 7/1991 Howland
5,034,013 A 7/1991 Kyle et al.
5,035,697 A 7/1991 Frigg
5,041,118 A 8/1991 Wasilewski
5,053,035 A 10/1991 McLaren
5,059,193 A 10/1991 Kuslich
5,066,296 A 11/1991 Chapman et al.
5,098,434 A 3/1992 Serbousek
5,102,414 A 4/1992 Kirsch
5,108,397 A 4/1992 White
5,122,141 A 6/1992 Simpson et al.
5,139,498 A 8/1992 Astudillo Ley
5,139,500 A 8/1992 Schwartz
5,147,367 A 9/1992 Ellis
5,147,402 A 9/1992 Bohler et al.
5,190,551 A 3/1993 Chin et al.
5,197,961 A 3/1993 Castle
5,242,444 A 9/1993 MacMillan
5,298,254 A 3/1994 Prewett et al.
5,334,205 A 8/1994 Cain
5,380,325 A 1/1995 Lahille et al.
5,390,683 A 2/1995 Pisharodi
5,433,718 A 7/1995 Brinker
5,443,466 A 8/1995 Shah
5,458,638 A 10/1995 Kuslich et al.
5,470,334 A 11/1995 Ross et al.
5,480,402 A 1/1996 Kim
5,569,249 A 10/1996 James et al.
5,591,235 A 1/1997 Kuslich
5,593,409 A 1/1997 Michelson
5,607,424 A 3/1997 Tropiano
5,609,635 A 3/1997 Michelson
5,609,636 A 3/1997 Kohrs et al.
5,626,616 A 5/1997 Speece
5,643,264 A 7/1997 Sherman et al.
5,645,599 A 7/1997 Samani
5,658,337 A 8/1997 Kohrs et al.
5,667,510 A 9/1997 Combs
5,669,909 A 9/1997 Zdeblick et al.
5,672,178 A 9/1997 Petersen
5,683,391 A 11/1997 Boyd
5,709,683 A 1/1998 Bagby
5,713,904 A 2/1998 Errico et al.
5,716,358 A 2/1998 Ochoa et al.
5,725,581 A 3/1998 Brånemark
5,743,912 A 4/1998 LaHille et al.
5,759,035 A 6/1998 Ricci
5,766,174 A 6/1998 Perry
5,766,252 A 6/1998 Henry et al.
5,766,261 A 6/1998 Neal et al.
5,788,699 A 8/1998 Bobst et al.
5,800,440 A 9/1998 Stead
5,868,749 A 2/1999 Reed
5,897,556 A 4/1999 Drewry et al.
5,899,906 A 5/1999 Schenk
5,928,239 A 7/1999 Mirza
5,941,885 A 8/1999 Jackson
5,961,522 A 10/1999 Mehdizadeh
5,961,554 A 10/1999 Janson et al.
6,010,507 A 1/2000 Rudloff
6,015,409 A 1/2000 Jackson
6,030,162 A 2/2000 Huebner et al.
6,053,916 A 4/2000 Moore
6,056,749 A 5/2000 Kuslich
6,066,175 A 5/2000 Henderson et al.
6,086,589 A 7/2000 Kuslich et al.
6,096,080 A 8/2000 Nicholson et al.
6,120,292 A 9/2000 Buser et al.
6,120,504 A 9/2000 Brumback et al.
6,129,730 A 10/2000 Bono et al.
6,143,031 A 11/2000 Knothe et al.
6,197,062 B1 3/2001 Fenlin
6,206,924 B1 3/2001 Timm
6,210,442 B1 4/2001 Wing et al.
6,214,049 B1 4/2001 Gayer et al.
6,221,074 B1 4/2001 Cole et al.
6,224,607 B1 5/2001 Michelson
6,241,732 B1 6/2001 Overaker et al.
6,264,657 B1 7/2001 Urbahns et al.
6,270,528 B1 8/2001 Mckay
6,287,343 B1 9/2001 Kuslich et al.
6,302,885 B1 10/2001 Essiger
6,302,914 B1 10/2001 Michelson
6,306,140 B1 10/2001 Siddiqui
6,319,253 B1 11/2001 Ackeret et al.
6,406,498 B1 6/2002 Tormala et al.
6,409,768 B1 6/2002 Tepic et al.
6,436,139 B1 8/2002 Shapiro et al.
6,451,020 B1 9/2002 Zucherman et al.
6,471,707 B1 10/2002 Miller et al.
6,485,518 B1 11/2002 Cornwall et al.
6,497,707 B1 12/2002 Bowman et al.

(56) References Cited

U.S. PATENT DOCUMENTS 6,517,541 B1 2/2003 Sesic
6,520,969 B2 2/2003 Lambrecht et al.
6,524,314 B1 2/2003 Dean et al.
6,527,775 B1 3/2003 Warburton
6,551,343 B1 4/2003 Törmälli et al.
6,556,857 B1 4/2003 Estes et al.
6,558,386 B1 5/2003 Cragg
6,565,566 B1 5/2003 Wagner et al.
6,575,899 B1 6/2003 Foley et al.
6,575,991 B1 6/2003 Chesbrough et al.
6,579,293 B1 6/2003 Chandran
6,582,431 B1 6/2003 Ray
6,582,467 B1 6/2003 Teitelbaum et al.
6,595,998 B2 7/2003 Johnson et al.
6,602,293 B1 8/2003 Biermann et al.
6,605,090 B1 8/2003 Trieu et al.
6,607,530 B1 8/2003 Carl et al.
6,620,163 B1 9/2003 Michelson
6,635,059 B2 10/2003 Randall et al.
6,666,868 B2 12/2003 Fallin
6,669,529 B1 12/2003 Scaries
6,673,075 B2 1/2004 Santilli
6,692,501 B2 2/2004 Michelson
6,712,852 B1 3/2004 Chung et al.
6,723,099 B1 4/2004 Goshert
6,723,100 B2 4/2004 Biedermann et al.
6,740,118 B2 5/2004 Eisermann et al.
6,743,257 B2 6/2004 Castro
D493,533 S 7/2004 Blain
6,793,656 B1 9/2004 Mathews
6,827,740 B1 12/2004 Michelson
6,984,235 B2 1/2006 Huebner
6,989,033 B1 1/2006 Schmidt
6,991,461 B2 1/2006 Gittleman
6,993,406 B1 1/2006 Cesarano et al.
7,018,416 B2 3/2006 Hanson et al.
7,118,579 B2 10/2006 Michelson
7,147,666 B1 12/2006 Grisoni
7,175,663 B1 2/2007 Stone
7,211,085 B2 5/2007 Michelson
7,223,269 B2 5/2007 Chappuis
7,300,439 B2 * 11/2007 May .................... A61B 17/866 606/86 A
7,314,488 B2 1/2008 Reiley
7,335,205 B2 2/2008 Aeschlimann et al.
7,338,500 B2 3/2008 Chappuis
7,396,365 B2 7/2008 Michelson
7,452,359 B1 11/2008 Michelson
7,452,369 B2 11/2008 Barry
7,481,831 B2 1/2009 Bonutti
7,527,649 B1 5/2009 Blain
7,534,254 B1 5/2009 Michelson
7,537,616 B1 5/2009 Branch et al.
7,569,054 B2 8/2009 Michelson
7,569,059 B2 8/2009 Cerundolo
7,601,155 B2 10/2009 Petersen
7,608,097 B2 10/2009 Kyle
7,608,098 B1 10/2009 Stone et al.
7,648,509 B2 1/2010 Stark
7,686,805 B2 3/2010 Michelson
7,699,852 B2 4/2010 Frankel et al.
7,708,761 B2 5/2010 Petersen
7,727,235 B2 6/2010 Contiliano et al.
7,758,646 B2 7/2010 Khandkar et al.
7,780,704 B2 8/2010 Markworth et al.
7,846,162 B2 12/2010 Nelson et al.
7,850,732 B2 12/2010 Heinz
7,857,832 B2 12/2010 Culbert et al.
7,887,565 B2 2/2011 Michelson
7,892,265 B2 2/2011 Perez-Cruet et al.
7,901,439 B2 3/2011 Horton
7,909,832 B2 3/2011 Michelson
7,922,765 B2 4/2011 Reiley
7,942,879 B2 5/2011 Christie et al.
7,951,176 B2 5/2011 Grady et al.
8,052,728 B2 11/2011 Hestad
8,062,365 B2 11/2011 Schwab
8,066,705 B2 11/2011 Michelson
8,066,709 B2 11/2011 Michelson
8,092,505 B2 1/2012 Sommers
8,142,481 B2 3/2012 Warnick
8,202,305 B2 6/2012 Reiley
8,221,499 B2 7/2012 Lazzara et al.
8,257,398 B2 9/2012 Jackson
8,268,099 B2 9/2012 O'Neill et al.
8,308,779 B2 11/2012 Reiley
8,308,783 B2 11/2012 Morris et al.
8,317,862 B2 11/2012 Troger et al.
8,348,950 B2 1/2013 Assell et al.
8,350,186 B2 1/2013 Jones et al.
8,353,932 B2 1/2013 Jackson
8,388,667 B2 3/2013 Reiley et al.
8,394,129 B2 3/2013 Morgenstern Lopez
8,398,635 B2 3/2013 Vaidya
8,398,682 B2 3/2013 Jackson et al.
8,414,648 B2 4/2013 Reiley
8,425,570 B2 4/2013 Reiley
8,430,930 B2 4/2013 Hunt
8,444,693 B2 5/2013 Reiley
8,449,585 B2 5/2013 Wallenstein et al.
8,467,851 B2 6/2013 Mire et al.
8,470,004 B2 6/2013 Reiley
8,475,505 B2 7/2013 Nebosky et al.
8,529,608 B2 9/2013 Terrill et al.
8,597,299 B2 12/2013 Farr et al.
8,608,802 B2 12/2013 Bagga et al.
D697,209 S 1/2014 Walthall et al.
8,641,737 B2 2/2014 Matthis et al.
8,641,766 B2 * 2/2014 Donner ................ A61B 17/846 606/279
8,663,298 B2 3/2014 Keyer et al.
8,663,332 B1 3/2014 To et al.
8,672,986 B2 3/2014 Klaue et al.
8,734,462 B2 5/2014 Reiley et al.
8,778,026 B2 7/2014 Mauldin
8,840,623 B2 9/2014 Reiley
8,840,651 B2 9/2014 Reiley
8,845,693 B2 9/2014 Smith et al.
8,858,601 B2 10/2014 Reiley
8,888,827 B2 11/2014 Harper et al.
8,894,685 B2 11/2014 Mickiewicz et al.
8,920,477 B2 12/2014 Reiley
8,926,670 B2 1/2015 Jackson
8,936,623 B2 1/2015 Jackson
8,945,190 B2 2/2015 Culbert et al.
8,945,193 B2 2/2015 Kirschman
8,951,254 B2 2/2015 Mayer et al.
8,951,293 B2 2/2015 Glazer et al.
8,951,295 B2 2/2015 Matityahu et al.
8,961,571 B2 2/2015 Lee et al.
8,979,911 B2 3/2015 Martineau et al.
8,986,348 B2 3/2015 Reiley
RE45,484 E 4/2015 Foley et al.
9,039,743 B2 5/2015 Reiley
9,044,321 B2 6/2015 Mauldin et al.
9,060,876 B1 6/2015 To et al.
9,113,972 B2 * 8/2015 Trudeau ............. A61B 17/8625
9,131,955 B2 9/2015 Swofford
9,149,286 B1 10/2015 Greenhalgh et al.
9,173,692 B1 11/2015 Kaloostian
9,198,676 B2 12/2015 Pilgeram et al.
9,220,535 B2 12/2015 Röbling et al.
9,314,286 B2 4/2016 Bottlang et al.
9,358,047 B2 6/2016 Mishra et al.
9,375,243 B1 6/2016 Vestgaarden
9,375,323 B2 6/2016 Reiley
9,445,852 B2 9/2016 Sweeney
9,486,264 B2 11/2016 Reiley et al.
9,492,201 B2 11/2016 Reiley
9,510,872 B2 12/2016 Donner et al.
9,526,548 B2 12/2016 Asfora
9,554,909 B2 1/2017 Donner
9,561,063 B2 2/2017 Reiley
9,566,100 B2 2/2017 Asfora

(56) References Cited

U.S. PATENT DOCUMENTS 9,603,613 B2 3/2017 Schoenefeld et al.
9,603,644 B2 3/2017 Sweeney
9,615,856 B2 4/2017 Arnett et al.
9,622,783 B2 4/2017 Reiley et al.
9,662,124 B2 5/2017 Assell et al.
9,662,128 B2 5/2017 Reiley
9,662,157 B2 5/2017 Schneider et al.
9,662,158 B2 5/2017 Reiley
9,675,394 B2 6/2017 Reiley
9,743,969 B2 8/2017 Reiley
9,757,154 B2 9/2017 Donner et al.
9,763,802 B2 9/2017 Baynham
9,775,648 B2 10/2017 Greenberg et al.
9,788,866 B2 10/2017 Jackson
9,808,292 B2 11/2017 Jackson
9,808,298 B2 11/2017 Stroncek et al.
9,808,299 B2 11/2017 Goel et al.
9,808,337 B2 11/2017 Housman et al.
9,820,789 B2 11/2017 Reiley
9,839,448 B2 12/2017 Reckling et al.
9,848,889 B2 12/2017 Taylor et al.
9,848,892 B2 12/2017 Biedermann et al.
9,883,874 B1 2/2018 Vestgaarden
9,888,911 B2 2/2018 Siegal
9,936,983 B2 4/2018 Mesiwala et al.
9,949,776 B2 4/2018 Mobasser et al.
9,949,843 B2 4/2018 Reiley et al.
9,956,013 B2 5/2018 Reiley et al.
9,993,276 B2 6/2018 Russell
9,993,277 B2 6/2018 Krinke et al.
9,999,449 B2 6/2018 Bonutti
10,004,547 B2 6/2018 Reiley
10,034,676 B2 7/2018 Donner
10,058,430 B2 8/2018 Donner et al.
10,166,033 B2 1/2019 Reiley et al.
10,179,014 B1 1/2019 Menmuir et al.
10,188,403 B2 1/2019 Mirochinik et al.
10,194,951 B2 2/2019 Jackson et al.
10,194,962 B2 2/2019 Schneider et al.
10,201,427 B2 2/2019 Mauldin et al.
10,219,885 B2 3/2019 Mamo et al.
10,245,044 B2 4/2019 Petersen
10,245,076 B2 4/2019 Fitzpatrick
10,245,087 B2 4/2019 Donner et al.
10,258,380 B2 4/2019 Sinha
10,271,882 B2 4/2019 Biedermann et al.
10,278,737 B2 5/2019 Smith
10,314,630 B2 * 6/2019 Trudeau ............. A61B 17/7055
10,321,937 B2 6/2019 Cormier et al.
10,321,945 B2 6/2019 Schifano et al.
10,335,200 B2 7/2019 Jackson
10,335,204 B2 7/2019 Matthis et al.
10,335,206 B2 7/2019 Nichols et al.
10,335,211 B2 7/2019 Chan et al.
10,335,212 B2 7/2019 Paolino et al.
10,335,216 B2 7/2019 Mari et al.
10,342,586 B2 7/2019 Schneider
10,349,983 B2 7/2019 Purcell et al.
10,357,287 B2 7/2019 Schlaepfer et al.
10,363,070 B2 7/2019 Jackson et al.
10,363,140 B2 7/2019 Mauldin et al.
10,368,919 B2 8/2019 Pham et al.
10,426,533 B2 10/2019 Mauldin et al.
10,426,539 B2 10/2019 Schifano et al.
10,433,880 B2 10/2019 Donner et al.
10,441,319 B2 10/2019 Jackson et al.
10,478,227 B2 11/2019 Leff et al.
10,517,734 B2 12/2019 Donner
10,596,003 B2 3/2020 Donner et al.
10,603,087 B2 3/2020 Brenzel et al.
10,610,370 B2 4/2020 Baynham
10,653,454 B2 5/2020 Frey et al.
10,653,544 B2 5/2020 Forsell
10,682,150 B2 6/2020 Stark
10,729,475 B2 8/2020 Childs
10,792,074 B2 10/2020 Jackson
10,799,367 B2 10/2020 Vrionis et al.
10,959,758 B2 3/2021 Mesiwala et al.
10,993,757 B2 5/2021 Schifano et al.
11,051,856 B2 7/2021 Jackson
11,071,573 B2 7/2021 Schneider et al.
11,116,519 B2 9/2021 Sand et al.
11,147,591 B2 10/2021 Jackson
11,147,597 B2 10/2021 Jackson
11,147,688 B2 10/2021 Reckling et al.
11,172,939 B2 11/2021 Donner et al.
11,234,830 B2 2/2022 Mesiwala et al.
11,291,485 B2 4/2022 Mauldin et al.
D951,455 S 5/2022 Ginn
11,337,821 B2 5/2022 Mauldin et al.
11,369,419 B2 6/2022 Mesiwala et al.
11,446,069 B2 9/2022 Mauldin et al.
11,471,286 B2 10/2022 Mauldin et al.
11,478,287 B2 10/2022 Mauldin et al.
D972,137 S 12/2022 Schifano et al.
11,571,245 B2 2/2023 Stuart et al.
11,607,251 B2 3/2023 Albert et al.
11,633,292 B2 4/2023 Reiley
11,672,570 B2 6/2023 Stuart et al.
11,672,664 B2 6/2023 Mauldin et al.
11,678,997 B2 6/2023 Mesiwala et al.
11,684,378 B2 6/2023 Reiley et al.
11,752,011 B2 9/2023 Stuart et al.
11,806,197 B2 11/2023 Frey et al.
11,850,156 B2 12/2023 Mauldin et al.
11,877,756 B2 1/2024 Sand et al.
11,980,399 B2 5/2024 Mesiwala et al.
11,986,397 B2 5/2024 Reiley
12,004,961 B2 6/2024 Reiley
12,023,079 B2 7/2024 Mauldin et al.
12,042,402 B2 7/2024 Stuart et al.
12,076,251 B2 9/2024 Mesiwala et al.
12,083,026 B2 9/2024 Reckling et al.
12,245,795 B2 3/2025 Spangler et al.
12,262,918 B2 4/2025 Yacoub et al.
12,427,027 B2 9/2025 Ginn
12,465,499 B2 11/2025 Spann
2001/0012942 A1 8/2001 Estes et al.
2001/0046518 A1 11/2001 Sawhney
2001/0047207 A1 11/2001 Michelson
2001/0049529 A1 12/2001 Cachia et al.
2002/0019637 A1 2/2002 Frey et al.
2002/0029043 A1 3/2002 Ahrens et al.
2002/0038123 A1 3/2002 Visotsky et al.
2002/0049497 A1 4/2002 Mason
2002/0077641 A1 6/2002 Michelson
2002/0082598 A1 6/2002 Teitelbaum
2002/0120275 A1 8/2002 Schmieding et al.
2002/0120335 A1 8/2002 Angelucci et al.
2002/0128652 A1 9/2002 Ferree
2002/0143334 A1 10/2002 von Hoffmann et al.
2002/0143335 A1 10/2002 von Hoffmann et al.
2002/0151903 A1 10/2002 Takel et al.
2002/0169507 A1 11/2002 Malone
2002/0183858 A1 12/2002 Contiliano et al.
2002/0198527 A1 12/2002 Mückter
2003/0018336 A1 1/2003 Vandewalle
2003/0032961 A1 2/2003 Pelo et al.
2003/0050642 A1 3/2003 Schmieding et al.
2003/0065332 A1 4/2003 TenHuisen et al.
2003/0074000 A1 4/2003 Roth et al.
2003/0078660 A1 4/2003 Clifford et al.
2003/0083668 A1 5/2003 Rogers et al.
2003/0083688 A1 5/2003 Simonson
2003/0088251 A1 5/2003 Braun et al.
2003/0097131 A1 5/2003 Schon et al.
2003/0139815 A1 7/2003 Grooms et al.
2003/0181979 A1 9/2003 Ferree
2003/0181982 A1 9/2003 Kuslich
2003/0199983 A1 10/2003 Michelson
2003/0229358 A1 12/2003 Errico et al.
2003/0233146 A1 12/2003 Grinberg et al.
2003/0233147 A1 12/2003 Nicholson et al.
2004/0010315 A1 1/2004 Song

(56) References Cited

U.S. PATENT DOCUMENTS

2004/0024458 A1 2/2004 Senegas et al.
2004/0034422 A1 2/2004 Errico et al.
2004/0073216 A1 4/2004 Lieberman
2004/0073314 A1 4/2004 White et al.
2004/0082955 A1 4/2004 Zirkle
2004/0087948 A1 5/2004 Suddaby
2004/0097927 A1 5/2004 Yeung et al.
2004/0106925 A1 6/2004 Culbert
2004/0117022 A1 6/2004 Marnay et al.
2004/0127990 A1 7/2004 Bartish, Jr. et al.
2004/0138750 A1 7/2004 Mitchell
2004/0138753 A1 7/2004 Ferree
2004/0147929 A1 7/2004 Biedermann et al.
2004/0158324 A1 8/2004 Lange
2004/0176287 A1 9/2004 Harrison et al.
2004/0176853 A1 9/2004 Sennett et al.
2004/0181282 A1 9/2004 Zucherman et al.
2004/0186572 A1 9/2004 Lange et al.
2004/0210221 A1 10/2004 Kozak et al.
2004/0225360 A1 11/2004 Malone
2004/0230305 A1 11/2004 Gorensek et al.
2004/0260286 A1 12/2004 Ferree
2004/0267369 A1 12/2004 Lyons et al.
2005/0015059 A1 1/2005 Sweeney
2005/0015146 A1 1/2005 Louis et al.
2005/0033435 A1 2/2005 Belliard et al.
2005/0037319 A1 2/2005 Bulard et al.
2005/0049590 A1 3/2005 Alleyne et al.
2005/0055023 A1 3/2005 Sohngen et al.
2005/0070905 A1 3/2005 Donnelly et al.
2005/0070907 A1 3/2005 Abernathie
2005/0071004 A1 3/2005 Re et al.
2005/0075641 A1 4/2005 Singhatat et al.
2005/0080415 A1 4/2005 Keyer et al.
2005/0107878 A1 5/2005 Conchy
2005/0112397 A1 5/2005 Rolfe et al.
2005/0113919 A1 5/2005 Cragg et al.
2005/0124993 A1 6/2005 Chappuis
2005/0131409 A1 6/2005 Chervitz et al.
2005/0137605 A1 6/2005 Assell et al.
2005/0143837 A1 6/2005 Ferree
2005/0149192 A1 7/2005 Zucherman et al.
2005/0158149 A1 7/2005 Panasik et al.
2005/0159749 A1 7/2005 Levy et al.
2005/0159812 A1 7/2005 Dinger et al.
2005/0165398 A1 7/2005 Reiley
2005/0192572 A1 9/2005 Abdelgany et al.
2005/0216017 A1 9/2005 Fielding
2005/0216082 A1 9/2005 Wilson et al.
2005/0228384 A1 10/2005 Zucherman et al.
2005/0228388 A1 10/2005 Brodke et al.
2005/0246021 A1 11/2005 Ringeisen et al.
2005/0251146 A1 11/2005 Martz et al.
2005/0273101 A1 12/2005 Schumacher
2005/0277940 A1 12/2005 Neff
2006/0004396 A1 1/2006 Easley et al.
2006/0025771 A1 2/2006 Jackson
2006/0036247 A1 2/2006 Michelson
2006/0036251 A1 2/2006 Reiley
2006/0036252 A1 2/2006 Baynham et al.
2006/0054171 A1 3/2006 Dall
2006/0058793 A1 3/2006 Michelson
2006/0058800 A1 3/2006 Ainsworth et al.
2006/0062825 A1 3/2006 Maccecchini
2006/0084986 A1 4/2006 Grinberg et al.
2006/0089644 A1 4/2006 Felix
2006/0089656 A1 4/2006 Allard et al.
2006/0095038 A1 5/2006 Jackson
2006/0111779 A1 5/2006 Petersen
2006/0129247 A1 6/2006 Brown et al.
2006/0142772 A1 6/2006 Ralph et al.
2006/0161163 A1 7/2006 Shino
2006/0178673 A1 8/2006 Curran
2006/0195094 A1* 8/2006 McGraw ............ A61B 17/7098 606/279
2006/0217717 A1 9/2006 Whipple
2006/0235387 A1 10/2006 Peterman
2006/0241600 A1 10/2006 Ensign et al.
2006/0241776 A1 10/2006 Brown et al.
2006/0271054 A1 11/2006 Sucec et al.
2006/0293662 A1 12/2006 Boyer, II et al.
2007/0027544 A1 2/2007 McCord et al.
2007/0038219 A1 2/2007 Matthis et al.
2007/0049933 A1 3/2007 Ahn et al.
2007/0066977 A1 3/2007 Assell et al.
2007/0073295 A1 3/2007 Biederman et al.
2007/0083265 A1 4/2007 Malone
2007/0088362 A1 4/2007 Bonutti et al.
2007/0093841 A1 4/2007 Hoogland
2007/0093898 A1 4/2007 Schwab et al.
2007/0106383 A1 5/2007 Abdou
2007/0149976 A1 6/2007 Hale et al.
2007/0156144 A1 7/2007 Ulrich et al.
2007/0156241 A1 7/2007 Reiley et al.
2007/0156246 A1 7/2007 Meswania et al.
2007/0161985 A1 7/2007 Demakas et al.
2007/0161989 A1 7/2007 Heinz et al.
2007/0173820 A1 7/2007 Trieu
2007/0219634 A1 9/2007 Greenhalgh et al.
2007/0233080 A1 10/2007 Na et al.
2007/0233146 A1 10/2007 Henniges et al.
2007/0233247 A1 10/2007 Schwab
2007/0250166 A1 10/2007 McKay
2007/0270833 A1 11/2007 Bonutti et al.
2007/0270858 A1 11/2007 Trieu et al.
2007/0270879 A1 11/2007 Isaza et al.
2007/0276500 A1 11/2007 Zucherman et al.
2007/0282443 A1 12/2007 Globerman et al.
2008/0021454 A1 1/2008 Chao et al.
2008/0021455 A1 1/2008 Chao et al.
2008/0021456 A1 1/2008 Gupta et al.
2008/0021461 A1 1/2008 Barker et al.
2008/0021480 A1 1/2008 Chin et al.
2008/0065093 A1 3/2008 Assell et al.
2008/0065215 A1 3/2008 Reiley
2008/0071356 A1 3/2008 Greenhalgh et al.
2008/0109083 A1 5/2008 Van Hoeck et al.
2008/0125868 A1 5/2008 Branemark et al.
2008/0132901 A1 6/2008 Recoules-Arche et al.
2008/0140082 A1 6/2008 Erdem et al.
2008/0147079 A1 6/2008 Chin et al.
2008/0154314 A1 6/2008 McDevitt
2008/0154374 A1 6/2008 Labrom
2008/0161810 A1 7/2008 Melkent
2008/0161927 A1 7/2008 Savage et al.
2008/0183204 A1 7/2008 Greenhalgh et al.
2008/0234758 A1 9/2008 Fisher et al.
2008/0249579 A1 10/2008 Taylor
2008/0255562 A1 10/2008 Gil et al.
2008/0255618 A1 10/2008 Fisher et al.
2008/0255622 A1 10/2008 Mickiewicz et al.
2008/0255664 A1 10/2008 Hogendijk et al.
2008/0255666 A1 10/2008 Fisher et al.
2008/0255667 A1 10/2008 Horton
2008/0275454 A1 11/2008 Geibel
2008/0294202 A1 11/2008 Peterson et al.
2008/0306554 A1 12/2008 McKinley
2009/0012529 A1 1/2009 Blain et al.
2009/0018660 A1 1/2009 Roush
2009/0024174 A1* 1/2009 Stark ................. A61B 17/7055 606/321
2009/0036927 A1 2/2009 Vestgaarden
2009/0037148 A1 2/2009 Lin et al.
2009/0043393 A1 2/2009 Duggal et al.
2009/0082810 A1 3/2009 Bhatnagar et al.
2009/0082869 A1 3/2009 Slemker et al.
2009/0099602 A1 4/2009 Aflatoon
2009/0099610 A1 4/2009 Johnson et al.
2009/0105770 A1 4/2009 Berrevooets et al.
2009/0118771 A1 5/2009 Gonzalez-Hernandez
2009/0131986 A1 5/2009 Lee et al.
2009/0138053 A1 5/2009 Assell et al.
2009/0157119 A1 6/2009 Hale
2009/0163920 A1 6/2009 Hochschuler et al.

(56) References Cited

U.S. PATENT DOCUMENTS

2009/0171394 A1 7/2009 Adbou
2009/0187247 A1 7/2009 Metcalf, Jr. et al.
2009/0216238 A1 8/2009 Stark
2009/0259261 A1* 10/2009 Reiley ................ A61B 17/7055 606/329
2009/0270929 A1 10/2009 Suddaby
2009/0287254 A1 11/2009 Nayet et al.
2009/0312798 A1 12/2009 Varela
2009/0319043 A1 12/2009 McDevitt et al.
2009/0324678 A1 12/2009 Thorne et al.
2010/0003638 A1 1/2010 Collins et al.
2010/0022535 A1 1/2010 Lee et al.
2010/0076502 A1 3/2010 Guyer et al.
2010/0081107 A1 4/2010 Bagambisa et al.
2010/0094290 A1 4/2010 Vaidya
2010/0094295 A1 4/2010 Schnieders et al.
2010/0094420 A1 4/2010 Grohowski
2010/0106194 A1 4/2010 Bonutti et al.
2010/0106195 A1 4/2010 Serhan et al.
2010/0114174 A1 5/2010 Jones et al.
2010/0114317 A1 5/2010 Lambrecht et al.
2010/0131011 A1 5/2010 Stark
2010/0137990 A1 6/2010 Apatsidis et al.
2010/0145461 A1 6/2010 Landry et al.
2010/0160977 A1 6/2010 Gephart et al.
2010/0168798 A1 7/2010 Clineff
2010/0191292 A1 7/2010 DeMeo et al.
2010/0228301 A1 9/2010 Greenhalgh et al.
2010/0234890 A1 9/2010 Alamin et al.
2010/0262242 A1 10/2010 Chavatte et al.
2010/0268228 A1 10/2010 Petersen
2010/0280619 A1 11/2010 Yuan et al.
2010/0280622 A1 11/2010 Mckinley
2010/0286778 A1 11/2010 Eisermann et al.
2010/0298889 A1 11/2010 Wilberg et al.
2010/0331851 A1 12/2010 Huene
2010/0331893 A1 12/2010 Geist et al.
2011/0009869 A1 1/2011 Marino et al.
2011/0009966 A1 1/2011 Michelson
2011/0022089 A1 1/2011 Assell et al.
2011/0029019 A1 2/2011 Ainsworth et al.
2011/0040338 A1 2/2011 Jackson
2011/0040362 A1 2/2011 Godara et al.
2011/0046737 A1 2/2011 Teisen
2011/0060373 A1 3/2011 Russell et al.
2011/0060375 A1 3/2011 Bonutti
2011/0066190 A1 3/2011 Schaller et al.
2011/0082551 A1 4/2011 Kraus
2011/0093020 A1 4/2011 Wu
2011/0098747 A1 4/2011 Donner et al.
2011/0098816 A1 4/2011 Jacob et al.
2011/0098817 A1 4/2011 Eckhardt et al.
2011/0106175 A1 5/2011 Rezach
2011/0153018 A1 6/2011 Walters et al.
2011/0160866 A1 6/2011 Laurence et al.
2011/0178561 A1 7/2011 Roh
2011/0184417 A1 7/2011 Kitch et al.
2011/0184518 A1 7/2011 Trieu
2011/0184519 A1 7/2011 Trieu
2011/0184520 A1 7/2011 Trieu
2011/0196372 A1 8/2011 Murase
2011/0213432 A1 9/2011 Geist et al.
2011/0230966 A1 9/2011 Trieu
2011/0238074 A1 9/2011 Ek
2011/0238124 A1 9/2011 Richelsoph
2011/0238181 A1 9/2011 Trieu
2011/0245930 A1 10/2011 Alley et al.
2011/0257755 A1 10/2011 Bellemere et al.
2011/0264229 A1* 10/2011 Donner .............. A61B 17/1739 623/18.11
2011/0276098 A1 11/2011 Biedermann et al.
2011/0295272 A1 12/2011 Assell et al.
2011/0295370 A1 12/2011 Suh et al.
2011/0313471 A1 12/2011 McLean et al.
2011/0313532 A1 12/2011 Hunt
2011/0319995 A1 12/2011 Voellmicke et al.
2012/0004730 A1 1/2012 Castro
2012/0035667 A1 2/2012 Van Nortwick et al.
2012/0083887 A1 4/2012 Purcell et al.
2012/0095560 A1 4/2012 Donner
2012/0165872 A1 6/2012 Alamin et al.
2012/0179256 A1 7/2012 Reiley
2012/0191191 A1 7/2012 Trieu
2012/0215315 A1 8/2012 Hochschuler et al.
2012/0226318 A1 9/2012 Wenger et al.
2012/0253398 A1 10/2012 Metcalf et al.
2012/0271424 A1 10/2012 Crawford
2012/0277866 A1 11/2012 Kalluri et al.
2012/0296428 A1 11/2012 Donner
2012/0323285 A1 12/2012 Assell et al.
2013/0018427 A1 1/2013 Pham et al.
2013/0030456 A1 1/2013 Assell et al.
2013/0030529 A1 1/2013 Hunt
2013/0035727 A1 2/2013 Datta
2013/0053852 A1 2/2013 Greenhalgh et al.
2013/0053854 A1 2/2013 Schoenefeld et al.
2013/0053902 A1* 2/2013 Trudeau ............. A61B 17/8685 606/313
2013/0053963 A1 2/2013 Davenport
2013/0072984 A1 3/2013 Robinson
2013/0085535 A1 4/2013 Greenhalgh et al.
2013/0096683 A1 4/2013 Kube
2013/0116793 A1 5/2013 Kloss
2013/0123850 A1 5/2013 Schoenefeld et al.
2013/0123935 A1 5/2013 Hunt et al.
2013/0131678 A1 5/2013 Dahners
2013/0144343 A1 6/2013 Arnett et al.
2013/0158609 A1 6/2013 Mikhail et al.
2013/0172736 A1 7/2013 Abdou
2013/0197590 A1 8/2013 Assell et al.
2013/0203088 A1 8/2013 Baerlecken et al.
2013/0218215 A1 8/2013 Ginn et al.
2013/0218282 A1 8/2013 Hunt
2013/0231746 A1 9/2013 Ginn et al.
2013/0237988 A1 9/2013 Mauldin
2013/0245703 A1 9/2013 Warren et al.
2013/0245763 A1 9/2013 Mauldin
2013/0253595 A1 9/2013 Zucherman et al.
2013/0267836 A1 10/2013 Mauldin et al.
2013/0267961 A1 10/2013 Mauldin et al.
2013/0267989 A1 10/2013 Mauldin et al.
2013/0274890 A1 10/2013 McKay
2013/0325129 A1 12/2013 Huang
2014/0012334 A1 1/2014 Armstrong et al.
2014/0012340 A1 1/2014 Beck et al.
2014/0031934 A1 1/2014 Trieu
2014/0031935 A1 1/2014 Donner et al.
2014/0031938 A1 1/2014 Lechmann et al.
2014/0031939 A1 1/2014 Wolfe et al.
2014/0046380 A1 2/2014 Asfora
2014/0074175 A1 3/2014 Ehler et al.
2014/0088596 A1 3/2014 Assell et al.
2014/0088707 A1 3/2014 Donner et al.
2014/0094860 A1 4/2014 Reimels
2014/0121776 A1 5/2014 Hunt
2014/0135927 A1 5/2014 Pavlov et al.
2014/0142700 A1 5/2014 Donner et al.
2014/0172026 A1 6/2014 Biedermann et al.
2014/0172027 A1 6/2014 Biedermann et al.
2014/0200618 A1 7/2014 Donner et al.
2014/0207240 A1 7/2014 Stoffman et al.
2014/0257294 A1 9/2014 Gedet et al.
2014/0257408 A1 9/2014 Trieu et al.
2014/0276846 A1 9/2014 Mauldin et al.
2014/0276851 A1 9/2014 Schneider et al.
2014/0277139 A1 9/2014 Vrionis et al.
2014/0277165 A1 9/2014 Katzman et al.
2014/0277460 A1 9/2014 Schifano et al.
2014/0277462 A1 9/2014 Yerby et al.
2014/0277463 A1 9/2014 Yerby et al.
2014/0288649 A1 9/2014 Hunt
2014/0288650 A1 9/2014 Hunt
2014/0296982 A1 10/2014 Cheng
2014/0330382 A1 11/2014 Mauldin

(56) References Cited

U.S. PATENT DOCUMENTS

2014/0364917 A1 12/2014 Sandstrom et al.
2015/0147397 A1 5/2015 Altschuler
2015/0150683 A1 6/2015 Donner et al.
2015/0182268 A1 7/2015 Donner et al.
2015/0216566 A1 8/2015 Mikhail et al.
2015/0238203 A1 8/2015 Asfora
2015/0250513 A1 9/2015 Sainte
2015/0250611 A1 9/2015 Schifano et al.
2015/0250612 A1 9/2015 Schifano et al.
2015/0257892 A1 9/2015 Lechmann et al.
2015/0320469 A1 11/2015 Biedermann et al.
2016/0022429 A1 1/2016 Greenhalgh et al.
2016/0095711 A1 4/2016 Castro
2016/0184103 A1 6/2016 Fonte et al.
2016/0242912 A1 8/2016 Lindsey et al.
2016/0249940 A1 9/2016 Stark
2016/0287171 A1 10/2016 Sand et al.
2016/0324643 A1 11/2016 Donner et al.
2016/0374727 A1 12/2016 Greenhalgh et al.
2017/0014235 A1 1/2017 Jones et al.
2017/0128214 A1 5/2017 Mayer
2017/0135733 A1 5/2017 Donner et al.
2017/0135737 A1 5/2017 Krause
2017/0143513 A1 5/2017 Sandstrom et al.
2017/0209155 A1 7/2017 Petersen
2018/0036041 A1 2/2018 Pham et al.
2018/0042652 A1 2/2018 Mari et al.
2018/0228621 A1 8/2018 Reiley et al.
2018/0235643 A1 8/2018 Lins et al.
2018/0256232 A1 9/2018 Russell
2018/0296227 A1 10/2018 Meek et al.
2018/0360512 A1 12/2018 Mari
2019/0133613 A1 5/2019 Reiley et al.
2019/0247094 A1 8/2019 Yacoub et al.
2019/0298528 A1 10/2019 Lindsey et al.
2019/0298542 A1 10/2019 Kloss
2019/0343640 A1 11/2019 Donner et al.
2019/0343653 A1 11/2019 McKay
2019/0388228 A1 12/2019 Donner et al.
2020/0222195 A1 7/2020 Assell et al.
2020/0246158 A1 8/2020 Bergey
2020/0315666 A1 10/2020 Nichols et al.
2020/0345510 A1 11/2020 Reiley
2021/0228360 A1 7/2021 Hunt et al.
2021/0393408 A1 12/2021 Ginn
2021/0393409 A1 12/2021 Ginn
2022/0031474 A1 2/2022 Reckling et al.
2022/0117640 A1 4/2022 Schneider et al.
2022/0273447 A1 9/2022 Ginn
2022/0273448 A1 9/2022 Ginn et al.
2022/0280303 A1 9/2022 Mauldin et al.
2022/0296377 A1 9/2022 Ginn et al.
2022/0296378 A1 9/2022 Ginn
2022/0304813 A1 9/2022 Ginn et al.
2022/0304814 A1 9/2022 Ginn
2022/0409381 A1 12/2022 Ginn
2023/0000526 A1 1/2023 Follini et al.
2023/0000630 A1 1/2023 Ginn et al.
2023/0000631 A1 1/2023 Ginn et al.
2023/0076180 A1 3/2023 Schifano et al.
2023/0210667 A1 7/2023 Lindsey et al.
2023/0263554 A1 8/2023 Stuart et al.
2023/0270559 A1 8/2023 Mesiwala et al.
2023/0390078 A1 12/2023 Bergey et al.
2023/0404762 A1 12/2023 Ginn et al.
2024/0173146 A1 5/2024 Greenhalgh et al.
2024/0206885 A1 6/2024 Sand et al.
2024/0225667 A9 7/2024 Reiley et al.
2024/0238097 A1 7/2024 Mauldin et al.
2024/0261107 A1 8/2024 Ginn et al.
2024/0285410 A1 8/2024 Ginn et al.
2024/0366401 A1 11/2024 Bergey
2024/0374399 A1 11/2024 Stuart et al.
2024/0390151 A1 11/2024 Ginn et al.
2025/0009396 A1 1/2025 Vestgaarden
2025/0040972 A1 2/2025 Schneider et al.
2025/0161070 A1 5/2025 Sand et al.
2025/0177011 A1 6/2025 Stuart et al.
2025/0177168 A1 6/2025 Reckling et al.
2026/0041567 A1 2/2026 Spann

FOREIGN PATENT DOCUMENTS

CN 1909848 A 2/2007
CN 101795632 A 8/2010
CN 102361601 A 2/2012
CN 102429716 A 5/2012
DE 102011001264 A1 9/2012
DE 102012106336 A1 1/2014
EP 1287796 A1 3/2003
EP 2070481 B1 2/2012
EP 2796104 A1 10/2014
EP 2590576 B1 10/2015
EP 2749238 B1 3/2017
EP 2887899 B1 8/2017
EP 2341852 B1 8/2018
EP 2496162 B1 10/2018
EP 3616634 A1 3/2020
EP 2328495 B1 7/2020
EP 2408389 B1 4/2021
JP 59200642 A 11/1984
JP 05-176942 A 7/1993
JP 05184615 A 7/1993
JP 09149906 A 10/1997
JP 10-85231 A 4/1998
JP 11318931 A 11/1999
JP 2002509753 A 4/2002
JP 2003511198 A 3/2003
JP 2003533329 A 11/2003
JP 2003534046 A 11/2003
JP 2004121841 4/2004
JP 2004512895 4/2004
JP 2004516866 6/2004
JP 2006506181 2/2006
JP 2007535973 A 12/2007
JP 2008540036 A 11/2008
JP 2009000501 A 1/2009
JP 2009521990 A 6/2009
JP 2009533159 A 9/2009
JP 2010137016 A 6/2010
JP 2011041802 A 3/2011
JP 2011512939 A 4/2011
JP 2012030105 A 2/2012
JP 2014147820 A 8/2014
JP 2015510506 A 4/2015
JP 2015531282 A 11/2015
WO WO97/31517 A2 8/1997
WO WO01/17445 A1 3/2001
WO WO02/38054 5/2002
WO WO03/007839 A2 1/2003
WO WO04/02344 1/2004
WO WO2004/043277 A1 5/2004
WO WO2005/009729 A2 2/2005
WO WO2006/003316 1/2006
WO WO2006/023793 A2 3/2006
WO WO2006/074321 A2 7/2006
WO WO2006/116850 A1 11/2006
WO WO2008/153723 A1 12/2008
WO WO2009/025884 A2 2/2009
WO WO2009/029074 A1 3/2009
WO WO2010/105196 A1 9/2010
WO WO2011/010463 A1 1/2011
WO WO2011/110865 A2 9/2011
WO WO2011/124874 A1 10/2011
WO WO2011/149557 A1 12/2011
WO WO2012/015976 A1 2/2012
WO WO2012/048008 A1 4/2012
WO WO2013/000071 A1 1/2013
WO WO2013/052807 A2 4/2013
WO WO2013/119907 A1 8/2013
WO WO2013/134678 A1 9/2013
WO WO2014/145902 A1 9/2014

(56) References Cited

FOREIGN PATENT DOCUMENTS

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.
Eisner; New SI Joint Fusion System Cleared; Orthopedics This Week; Jun. 28, 2018; retreived from the internet <https://ryortho.com/breaking/new-si-joint-fusion-system-cleared/> on Sep. 8, 2022; 5 pages.
Khurana et al.; Percutaneous fusion of the sacroiliac joint with hollow modular anchorage screws, clinical and radiological outcome; J Bone Joint Surg; vol. 91-B; No. 5; pp. 627-631; May 2009.
Lu et al.; Mechanical properties of porous materials; Journal of Porous Materials; 6(4); pp. 359-368; Nov. 1, 1999.
Peretz et al.; The internal bony architecture of the sacrum; Spine; 23(9); pp. 971-974; May 1, 1998.
Richards et al.; Bone density and cortical thickness in normal, osteopenic, and osteoporotic sacra; Journal of Osteoporosis; 2010(ID 504078); 5 pgs; Jun. 9, 2010.
Wise et al., Minimally invasive sacroiliac arthrodesis, outcomes of a new technique; J Spinal Disord Tech; vol. 21; No. 8; pp. 579-584; Dec. 2008.
Third Party Observation; PCT/US2021/062337; Aug. 29, 2022; 6 pages.
Mesiwala et al.; U.S. Appl. No. 18/632,102 entitled "Implants for spinal fixation or fusion," filed Apr. 10, 2024.
Mesiwala et al.; U.S. Appl. No. 18/716,090 entitled "Fusion cages and methods for sacro-iliac joint stabilization," filed Jun. 3, 2024.
Stuart et al.; U.S. Appl. No. 18/805,412 entitled "Pelvic stabilization implants, methods of use and manufacture," filed Aug. 14, 2024.
Reckling et al.; U.S. Appl. No. 18/809,229 entitled "Sacro-iliac joint stabilizing implants and methods of implantation," filed Aug. 19, 2024.
Mesiwala et al.; U.S. Appl. No. 18/810,211 entitled "Implants for spinal fixation and or fusion," filed Aug. 20, 2024.
Sand et al.; U.S. Appl. No. 18/951,349 entitled "Systems, devices, and methods for preparing bone to receive an implant," filed Nov. 18, 2024.
Anderson Jr. et al.; U.S. Appl. No. 18/870,896 entitled "Bi-lateral pelvic stabilization," filed Dec. 2, 2024.
Polly et al.; U.S. Appl. No. 19/024,752 entitled "Spine stabilization," filed Jan. 16, 2025.
Follini et al.; U.S. Appl. No. 19/078,206 entitled "Threaded bone implant and systems," filed Mar. 12, 2025.

* cited by examiner

Bone Segment 1
Space or Joint
Bone Segment 2
44
48
44

210
208
206

Vertebra L4
Vertebra L5
Sacrum SI
Sacrum
Left Ilium
20
48
48
20
Femur
Femur

Vertebra L4
Vertebra L5
Sacrum SI
Sacrum
Left Ilium
20
Femur
Femur

FENESTRATED IMPLANT

CROSS REFERENCE TO RELATED APPLICATIONS

This application is a continuation of U.S. application Ser. No. 17/822,360, filed Aug. 25, 2022, now U.S. Pat. No. 12,023,079, which is a continuation of U.S. application Ser. No. 17/649,544, filed on Jan. 31, 2022, now U.S. Pat. No. 11,446,069, which is a continuation U.S. application Ser. No. 16/552,912, filed Aug. 27, 2019, now U.S. Pat. No. 11,291,485, which is a continuation of U.S. application Ser. No. 13/888,249, filed May 6, 2013, now U.S. Pat. No. 10,426,533, which claims the benefit of U.S. Provisional Application No. 61/642,681, filed May 4, 2012, titled "FENESTRATED IMPLANT", each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference. For example, this application incorporates by reference in their entireties U.S. Patent Publication No. 2011/0087294 and U.S. Patent Publication No. 2011/0118785.

FIELD

This application relates generally to implants used in medical procedures such as bone fixation or fusion. More specifically, this application relates to fenestrated implants used in bone fixation or fusion.

BACKGROUND

Many types of hardware are available both for the fixation of bones that are fractured and for the fixation of bones that are to be fused (arthrodesed).

For example, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and -the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion.

In order to promote bone growth into the implant and enhance fusion of the implant with the bone, pockets or channels can be created in the implant that promote bone growth into the implant. However, these pockets or channels may weaken the structural integrity of the implant, which can also be required to bear large stresses. Therefore, it would be desirable to provide an implant with pockets or channels to promote bone growth while substantially maintaining the structural integrity of the implant.

SUMMARY OF THE DISCLOSURE

The present invention relates generally to implants used in medical procedures such as bone fixation or fusion. More specifically, this application relates to fenestrated implants used in bone fixation or fusion.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, a central lumen extending along the longitudinal axis of the elongate body, and a plurality of holes with openings on the plurality of faces, wherein the holes are in fluid communication with the central lumen.

In some embodiments, the holes are circular. In some embodiments, the holes are oval. In some embodiments, the holes are arranged in a single longitudinal row on each face. In some embodiments, the holes are arranged in a plurality of longitudinal rows on each face.

In some embodiments, the elongate body is coated with a biologic aid.

In some embodiments, the holes have a diameter that is about equal to the diameter of the central lumen. In some embodiments, the holes have a diameter that is between about 0.2 to 0.5 of the width of the faces.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, a central lumen extending along the longitudinal axis of the elongate body, and a plurality of side pockets extending along a portion of each of the plurality of faces, wherein the side pockets have a depth that does not extend to the central lumen.

In some embodiments, each of the plurality of faces has only one side pocket. In some embodiments, each of the side pockets is centered on each of the faces. In some embodiments, the side pockets have a width that is between about 0.2 to 0.8 of the width of the faces and a length that is between about 0.5 to 0.9 of the length of the faces.

In some embodiments, the implant further includes a plurality of holes located within the side pockets, wherein the holes are in fluid communication with the central lumen.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, and a central lumen extending along the longitudinal axis of the elongate body, wherein each one of the plurality of apexes includes a groove that extends along the length of the apex.

In some embodiments, an implant for bone fixation is provided. The implant can include an elongate body having a longitudinal axis and a rectilinear cross section transverse to the longitudinal axis, a plurality of faces, a plurality of apexes joining the plurality of faces, and a central lumen extending along the longitudinal axis of the elongate body, wherein each one of the plurality of apexes includes a plurality of pockets located at discrete points along the length of each apex.

In some embodiments, an implant for bone fixation is provided. The implant can include an elongate body having a longitudinal axis, a distal end, a proximal end, and a rectilinear cross section transverse to the longitudinal axis, a plurality of faces, each face formed from a wall with a thickness between about 2 to 3 mm in thickness, and a plurality of fenestrations disposed on each face.

In some embodiments, the distal end of the elongate body is formed into one or more cutting edges.

In some embodiments, the rectilinear cross section has three sides. In some embodiments, the rectilinear cross section has four sides, such as in FIG. 8C.

In some embodiments, the fenestrations are located on a distal portion of the elongate body that is configured to be implanted within the sacrum of a patient while the proximal portion of the elongate body that is configured to be implanted within the illium is free from fenestrations.

In some embodiments, the fenestrations are arranged in a staggered pattern.

In some embodiments, the implant further includes a cap on the proximal end of the elongate body, the cap having a hole sized to receive a guide pin.

In some embodiments, the elongate body has an inner surface and an outer surface that are porous. In some embodiments, the elongate body has an inner surface and an outer surface that are roughened. In some embodiments, the elongate body has an inner surface and an outer surface that are plasma coated. In some embodiments, the elongate body has an inner surface and an outer surface that are coated with a biologic aid. In some embodiments, the biologic aid is a bone morphogenetic protein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2D are side section views of the formation of a broached bore in bone according to one embodiment of the invention.

FIGS. 5 to 7A and 7B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.

DETAILED DESCRIPTION

Figure 1A:
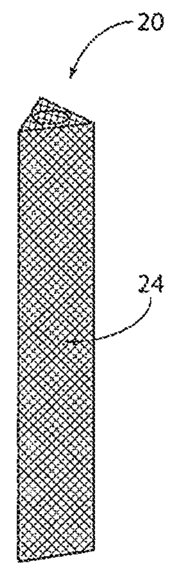
FIGS. 1A-1V illustrate various embodiments of implant structures with different fenestrations.
Figure 3:
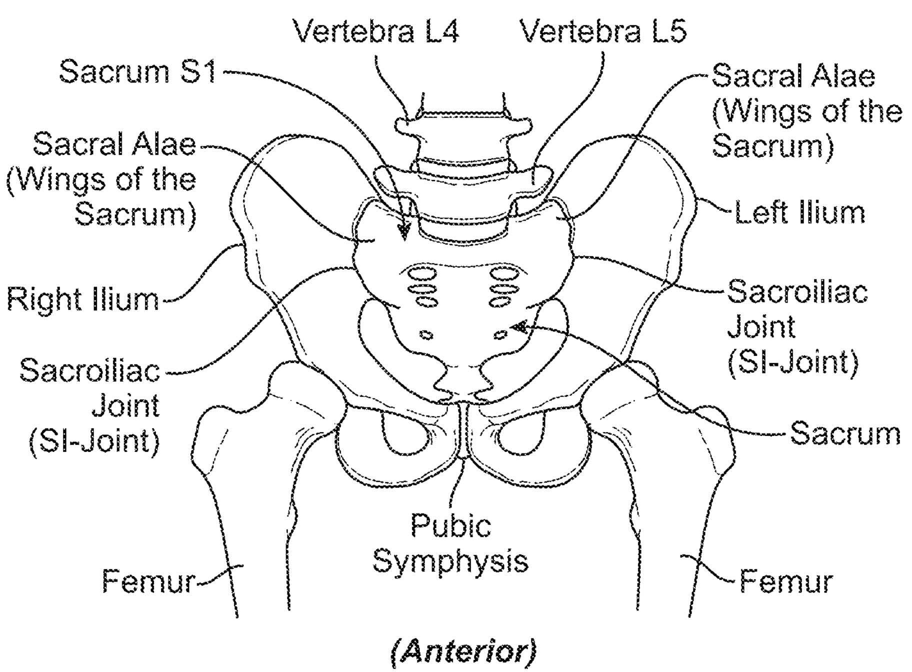
FIGS. 3 and 4 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 4:
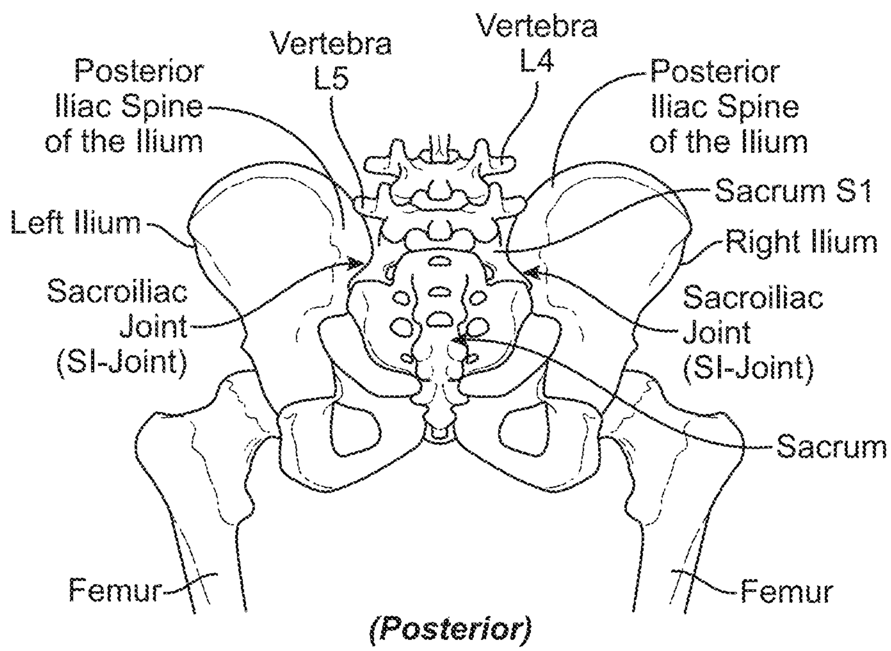

Elongated, stem-like implant structures 20 like that shown in FIG. 1A make possible the fixation of the SI-Joint (shown in anterior and posterior views, respectively, in FIGS. 3 and 4) in a minimally invasive manner. These implant structures 20 can be effectively implanted through the use of a lateral surgical approach. The procedure is desirably aided by conventional lateral and/or anterior-posterior (A-P) visualization techniques, e.g., using X-ray image intensifiers such as a C-arms or fluoroscopes to produce a live image feed that is displayed on a TV screen.

In some embodiments, the implant structures 20 can include pockets, pathways, cavities, openings, fenestrations, channels and/or recesses that allow bone graft materials to be incorporated into the implant structure. These bone graft materials can promote bone growth into and/or around the implant structure, which can reduce the time it takes for the implant structure to be stably integrated with the bone. Bone graft materials can be applied to and/or injected into the implant structure before implantation or applied after implantation by injection of the bone graft material into a proximal cannula or other conduit. In some embodiments, the surfaces of the implant structure 20 can be roughened or textured to promote bone growth and adherence of the bone graft materials. The internal and/or external surfaces can be roughened or textured by mechanical means or can be spray coated with a roughening material.

The bone graft materials can be a liquid, gel, slurry, paste, powder or other form, and can include a biologic aid that can promote and/or enhance bony ingrowth, tissue repair, and/or reduce inflammation, infection and pain. For example, the biologic aid can include growth factors, such as bone morphogenetic proteins (BMPs), hydroxyapatite in, for example, a liquid or slurry carrier, demineralized bone, morselized autograft or allograft bone, medications to reduce inflammation, infection or pain such as analgesics, antibiotics and steroids. In some embodiments, the growth factors can be human recombinant growth factors, such as hr-BMP-2 and/or hr-BMP-7, or any other human recombinant form of BMP, for example. The carrier for the biologic aid can be a liquid or gel such as saline or a collagen gel, for example. The biologic aid can also be encapsulated or incorporated in a controlled released formulation so that the biologic aid is released to the patient at the implant site over a longer duration. For example, the controlled release formulation can be configured to release the biologic aid over the course of days or weeks or months, and can be configured to release the biologic aid over the estimated time it would take for the implant site to heal. The amount of biologic aid delivered to the implant structure can be controlled using a variety of techniques, such as controlling or varying the amount of coating material applied to the implant and/or controlling or varying the amount of biologic aid incorporated into the coating material. In some embodiments, it may be important to control the amount of biologic aid delivered because excessive use of certain biologic aids can result in negative effects such as radicular pain, for example.

In general, any pockets, pathways, cavities, openings, fenestrations, channels and/or recesses in the implant structure may weaken its structural strength, including for example the bending and shear strengths. The following examples of implant structures are variations of the solid triangular implant structure 20 of FIG. 1A, which has a single central, longitudinally oriented lumen or cannula for receiving a guide wire or guide pin. The relative bending and shear strengths can be compared to the cannulated but otherwise solid implant structure 20 of FIG. 1A, which can be assigned a bending strength of 1.00 and a shear strength of 1.00. The relative bending and shear strengths can be modified or optimized for structural strength and ability to promote bone grafting by varying the size, number, spacing, location, orientation, and shape of the pockets, pathways, cavities, openings, fenestrations, channels and/or recesses. Although the embodiments illustrated herein show triangular implant structures, implant structures with different rectilinear shapes, such as rectangular or square, can be used or substituted for the triangular implant structures.

Figure 1B:
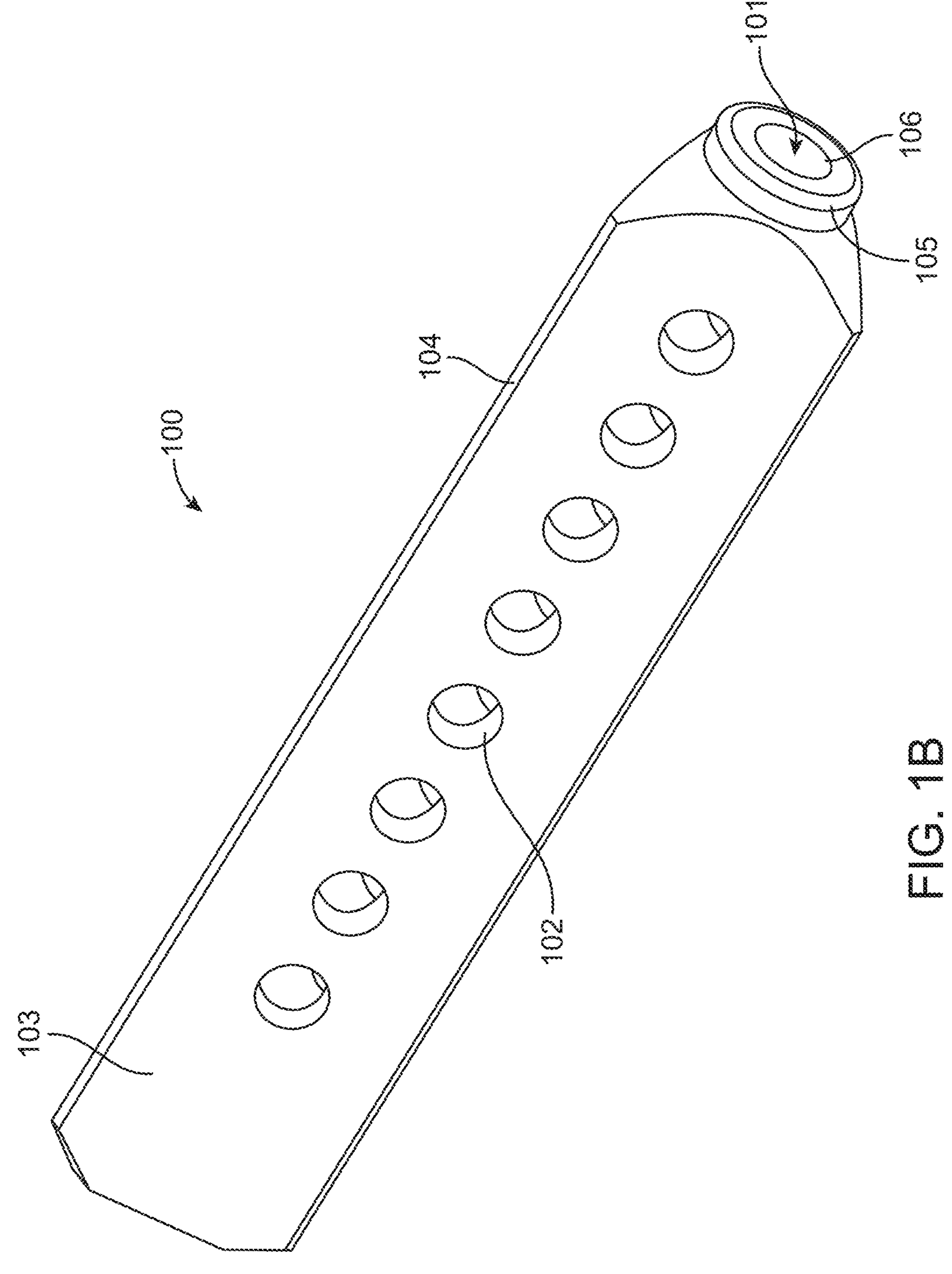
Figure 1C:
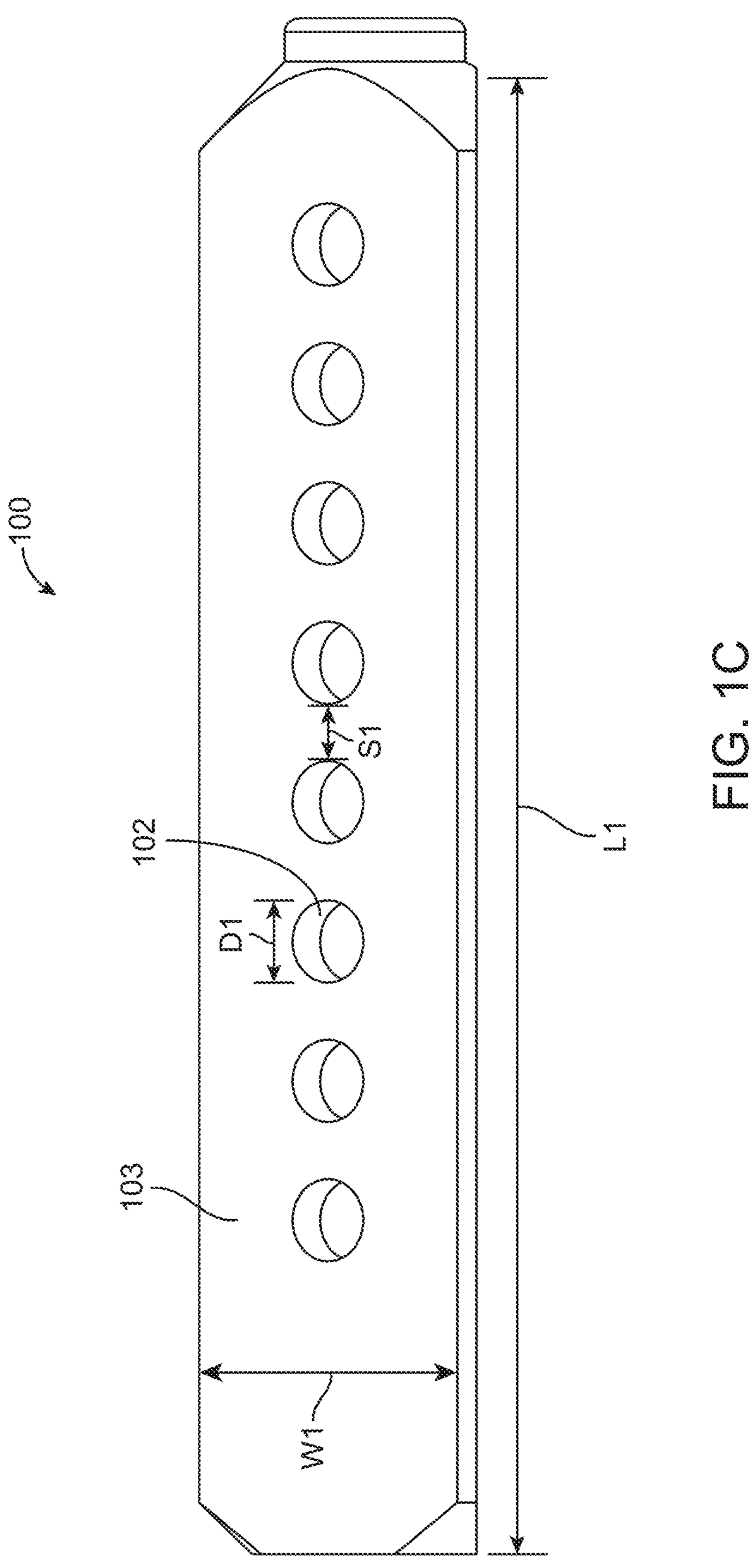
Figure 1D:
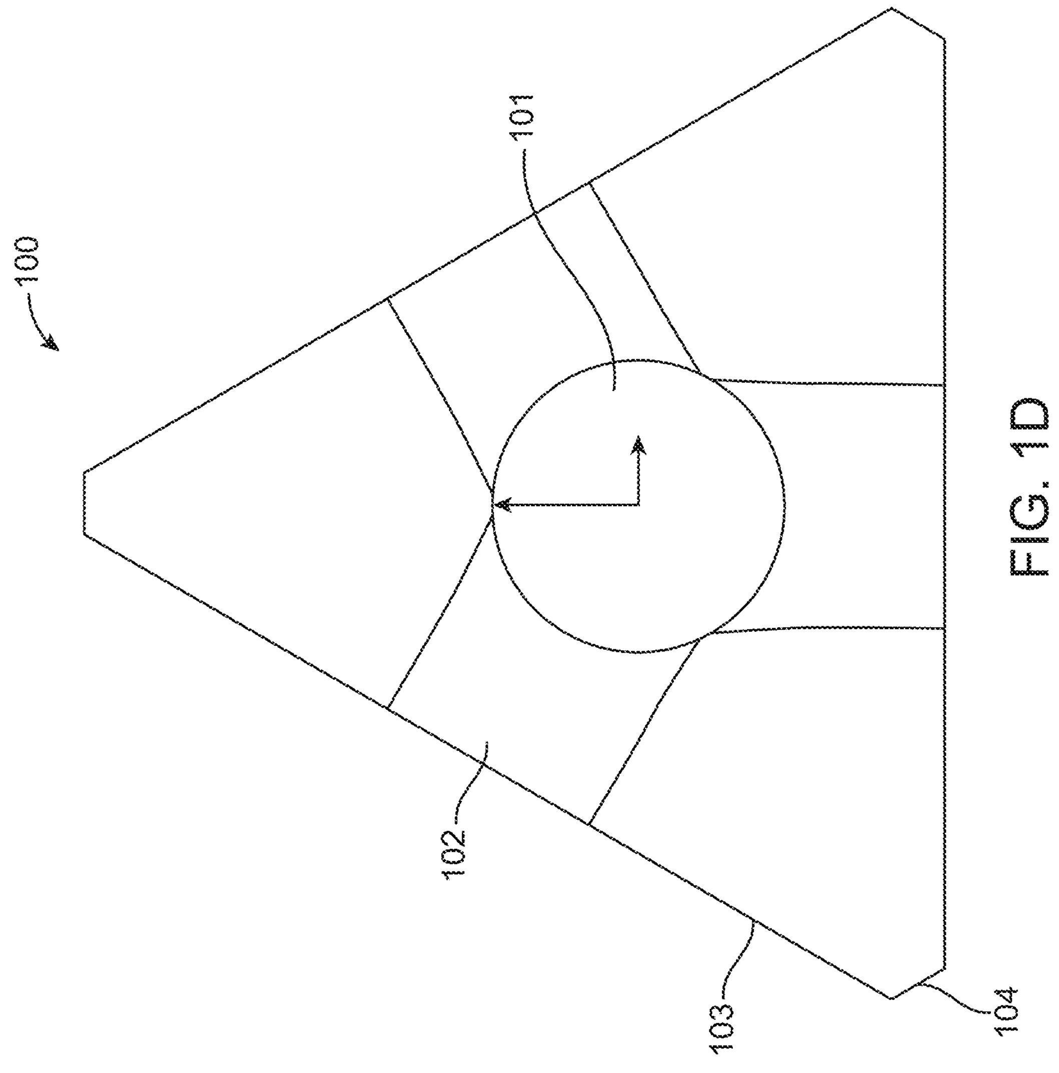

FIGS. 1B-Dillustrate an embodiment of a triangular implant structure 100 having a central lumen 101 and a series of holes 102 on each face 103 of the implant structure 100 that reach and provide access to the central lumen 101. The holes 102 can be centered on the face 103 and extend inwardly at an angle that is substantially perpendicular or normal to the face 103 of the implant structure 100. In some embodiments, each apex 104 can be beveled or rounded. In some embodiments, the distal end 105 of the implant structure 100 can be tapered to facilitate implantation into the bone. In some embodiments, the diameter of the holes 102 can be equal to or substantially equal to the diameter of the central lumen 101. In other embodiments, the diameter of the holes 102 can be greater than or less than the diameter of the central lumen 101. In some embodiments, the implant structure 100 illustrated in FIGS. 1B-D has a relative bending strength of about 0.82 and a relative shear strength of about 0.66. In some embodiments, to inject or load the implant structure 100 with bone graft materials, the distal hole 106 of the central lumen 101 can be blocked or sealed so that flow of the bone graft materials fills the central lumen 101 and exits the side holes 102.

In some embodiments, the holes 102 can have a diameter (D1) that is about 0.3 of width (W1) of the face 103 of the implant structure 100. In some embodiments, the holes 102 can have a diameter that is greater than about 0.3 of the width of the face 103 of the implant structure 100. In some embodiments, the holes 102 can have a diameter that is less than about 0.3 of the width of the face 103 of the implant structure 100. In some embodiments, the holes 102 can have a diameter that is between about 0.2 to about 0.5 of the width of the face 103 of the implant structure. In some embodiments, the holes 102 can be separated from adjacent holes 102 by about ⅔ of the hole diameter, where separation distance (S1) is measured by the distance between the circumference of the holes 102. In some embodiments, the holes 102 can be separated from adjacent holes 102 by less than about ⅔ of the hole diameter. In some embodiments, the holes 102 can be separated from adjacent holes 102 by greater than about ⅔ of the hole diameter. In some embodiments, the holes 102 can be separated from adjacent holes 102 by about 0.5 to about 2 times, or about 0.5 to about 1 times the hole 102 diameter. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1E:
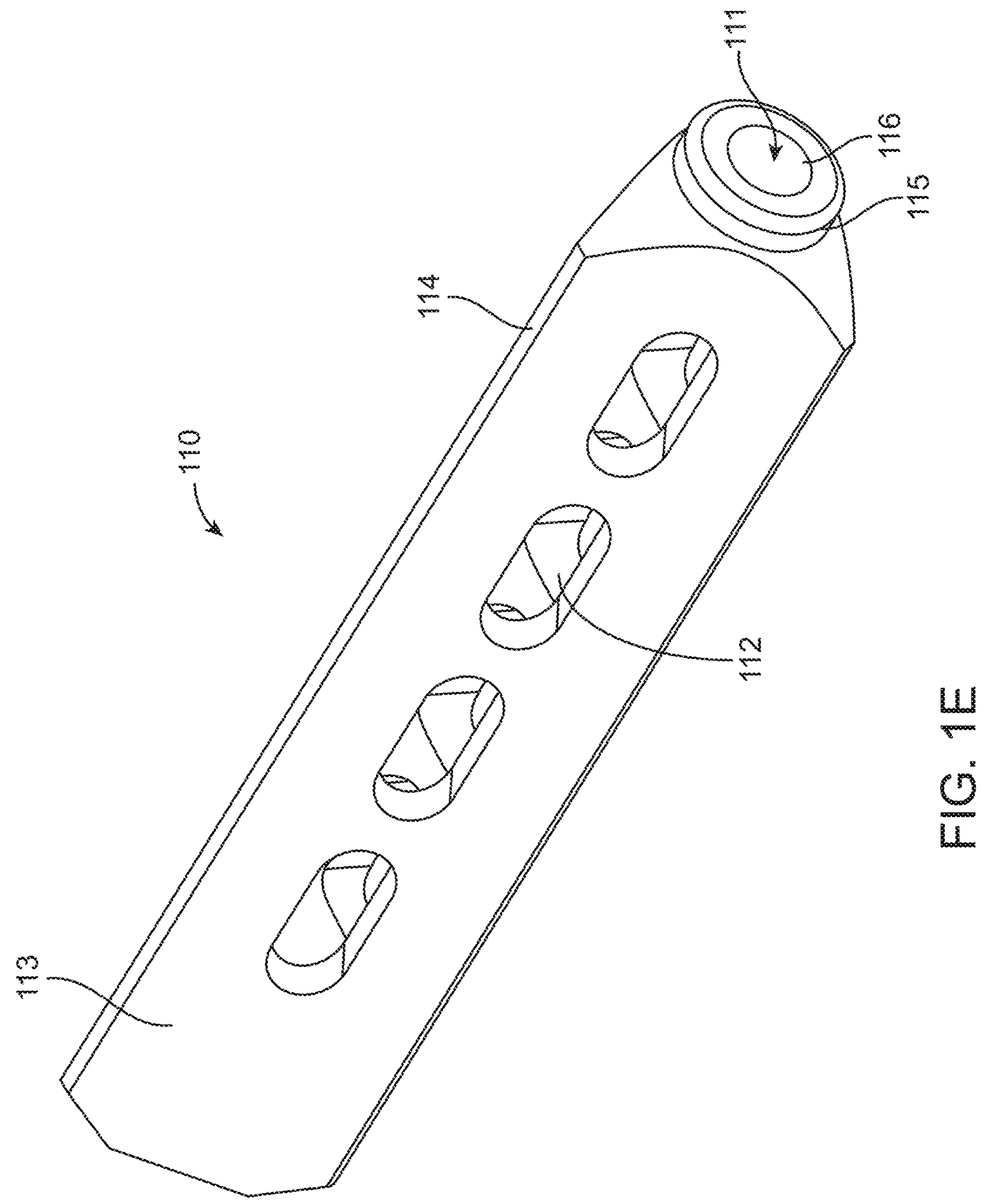
Figure 1F:
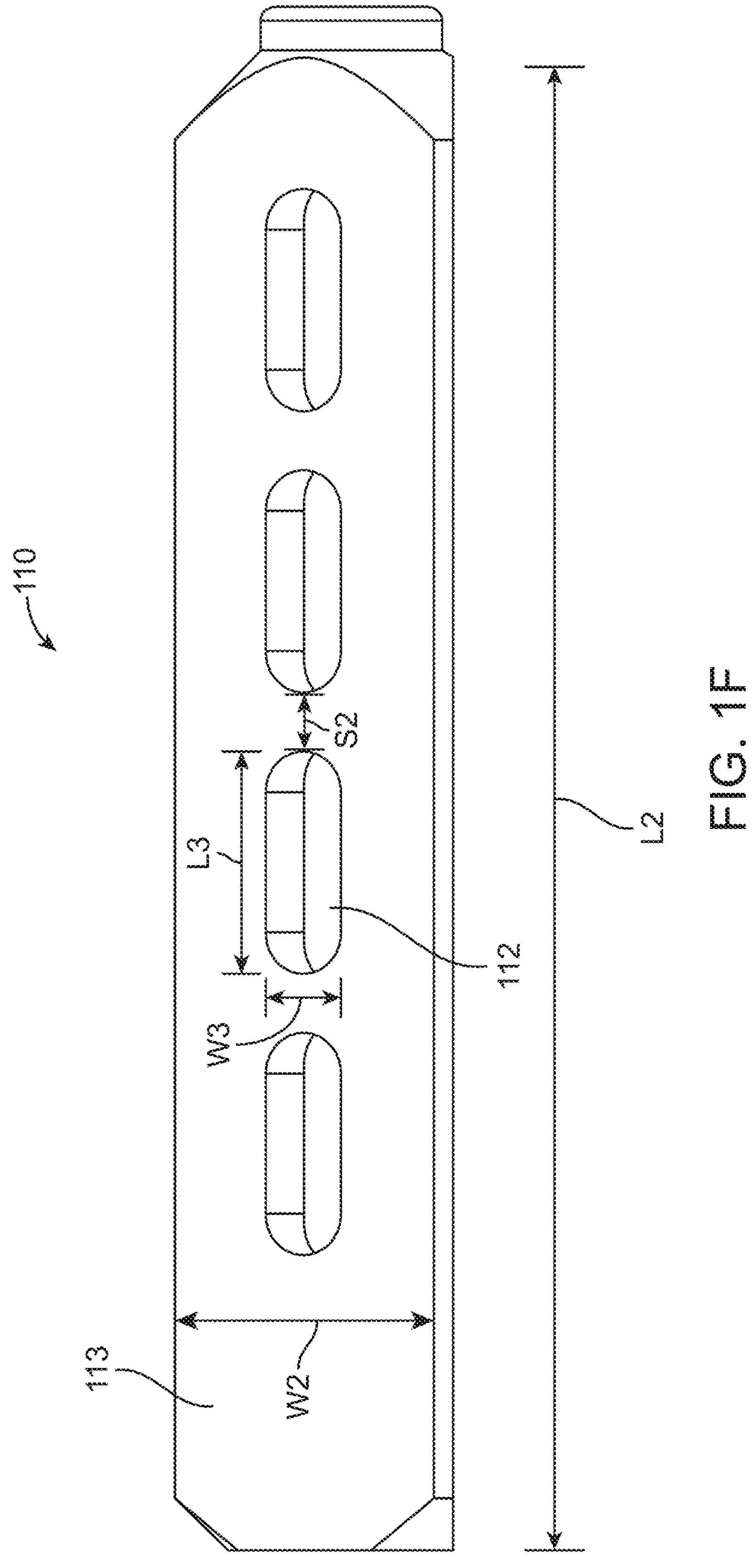
Figure 1G:
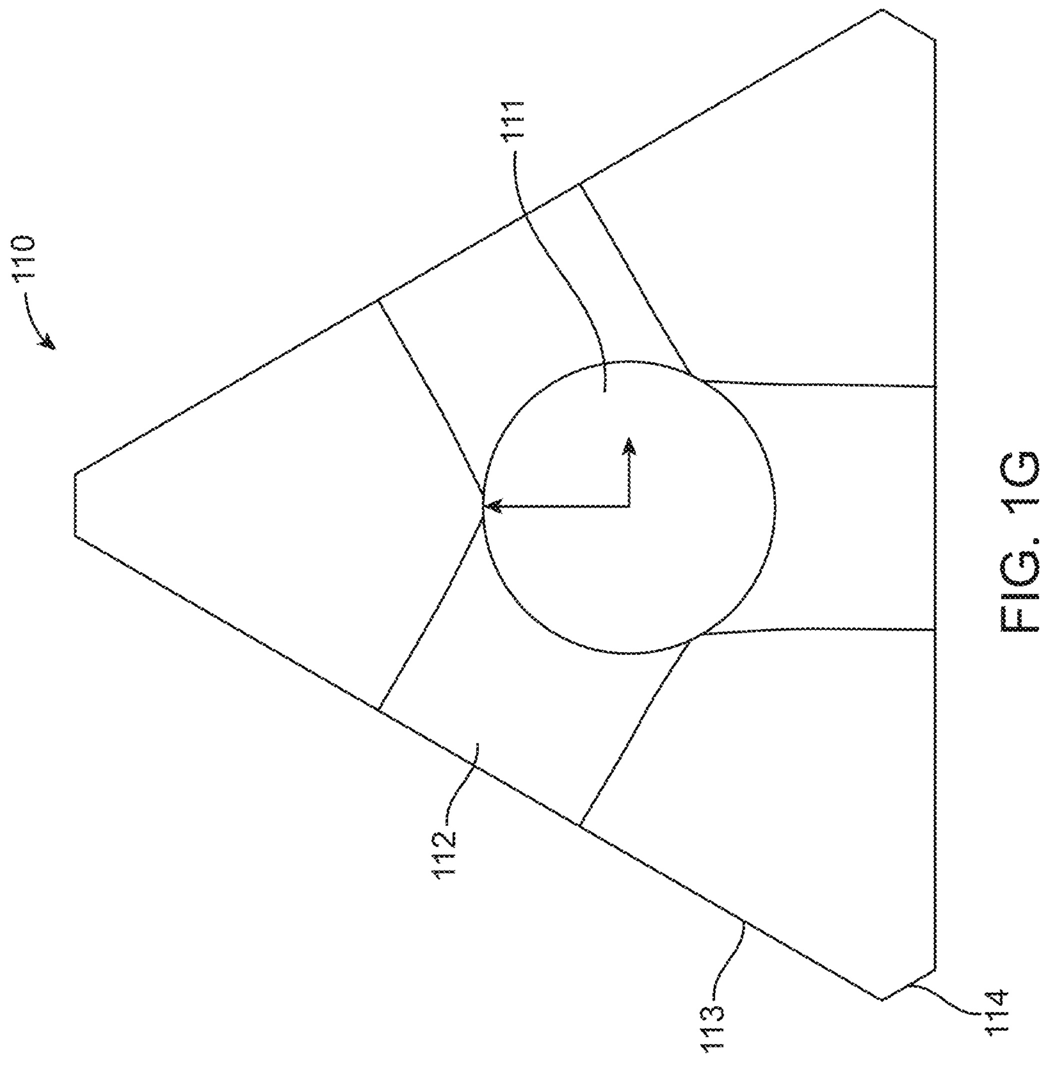

FIGS. 1E-G illustrate another embodiment of an implant structure 110 having a central lumen 111 and a series of slots 112 on each face 113 of the implant structure 110 that reach and provide access to the central lumen 111. The slots 112 can be centered on the face 113 and extend inwardly at an angle that is substantially perpendicular or normal to the face 113 of the implant structure 110. In some embodiments, each apex 114 can be beveled or rounded. In some embodiments, the distal end 115 of the implant structure 110 can be tapered to facilitate implantation into the bone. In some embodiments, the width of the slots can be equal to or substantially equal to the diameter of the central lumen 111. In other embodiments, the width of the slots can be greater than or less than the diameter of the central lumen 111. In some embodiments, the implant structure 110 illustrated in FIGS. 1E-G has a relative bending strength of about 0.82 and a relative shear strength of about 0.66. In some embodiments, to inject or load the implant structure 110 with bone graft materials, the distal hole 116 of the central lumen 111 can be blocked or sealed so that flow of the bone graft materials fills and exits the slots 112.

In some embodiments, the slots 112 can have a width (W3) that is about 0.3 of width (W2) of the face 113 of the implant structure 110. In some embodiments, the slots 112 can have a width that is greater than about 0.3 of the width of the face 113 of the implant structure 110. In some embodiments, the slots 112 can have a width that is less than about 0.3 of the width of the face 113 of the implant structure 110. In some embodiments, the slots 112 can have a width that is between about 0.2 to about 0.6 of the width of the face 113 of the implant structure 110. In some embodiments, the slots 112 can have a length (L3) that is about 0.15 the length (L2) of the face 113. In some embodiments, the slots 112 can have a length that is less than about 0.15 the length of the face 113. In some embodiments, the slots 112 can have a length that is greater than about 0.15 the length of the face 113. In some embodiments, the slots 112 can have a length that is between about 0.1 to 0.4, or about 0.1 to 0.25 the length of the face 113. In some embodiments, the slots 112 are separated (S2) from adjacent slots 112 by about ⅔ the width of the slot 112. In some embodiments, the slots 112 are separated from adjacent slots 112 by greater than about ⅔ the width of the slot 112. In some embodiments, the slots 112 are separated from adjacent slots 112 by less than about ⅔ the width of the slot 112. In some embodiments, the slots 112 can be separated from adjacent slots 112 by about 0.5 to about 2 times, or about 0.5 to about 1 times the slot 112 width. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1H:
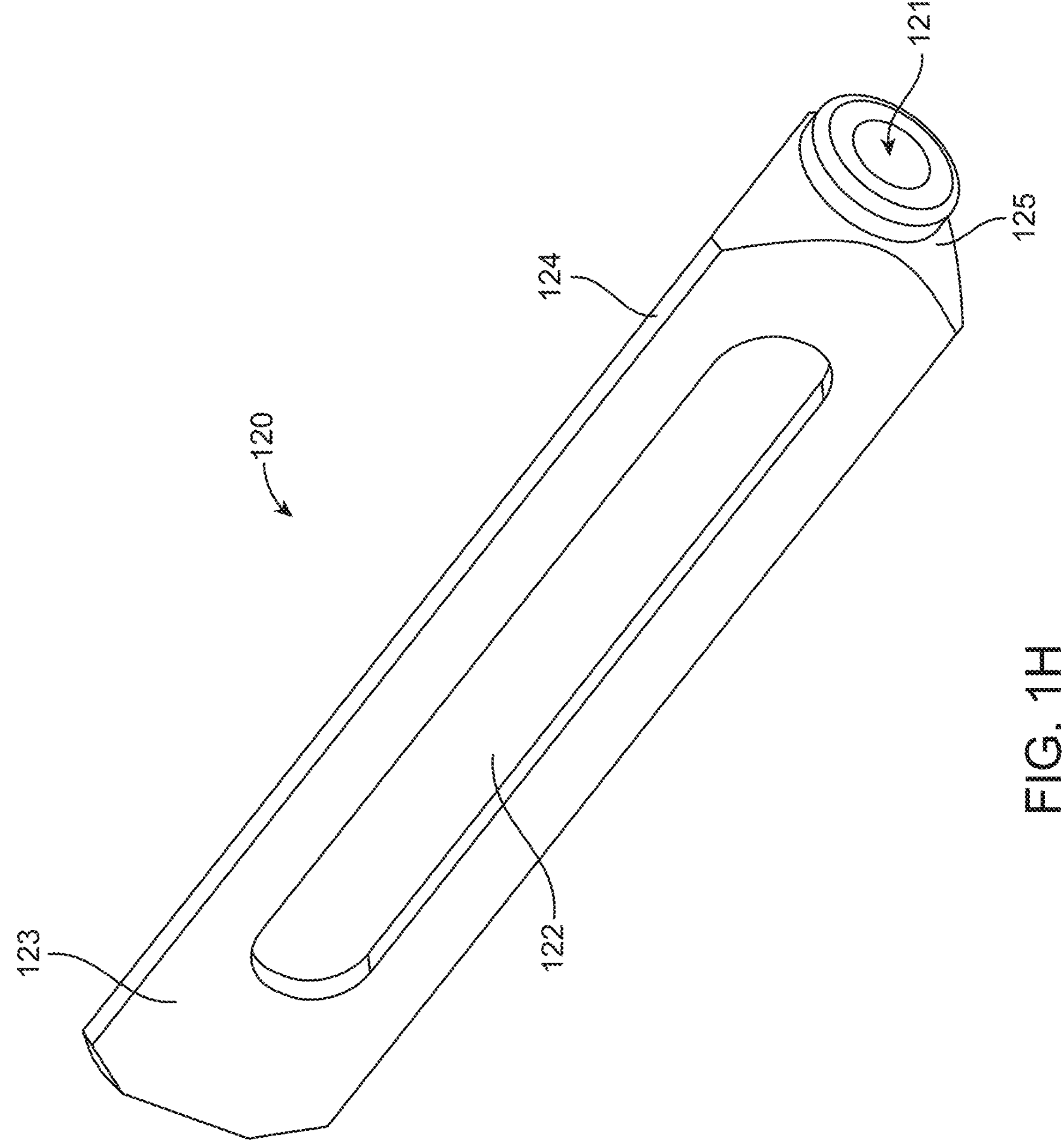
Figure 1I:
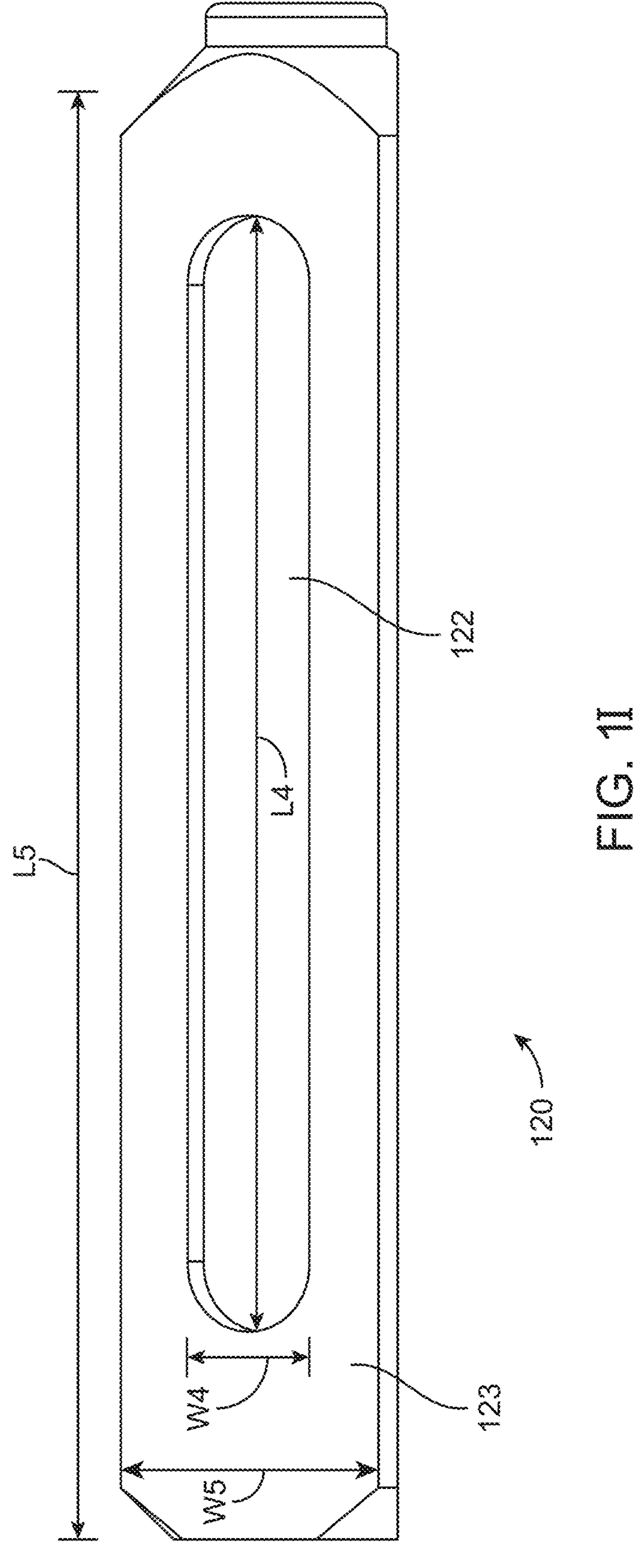
Figure 1J:
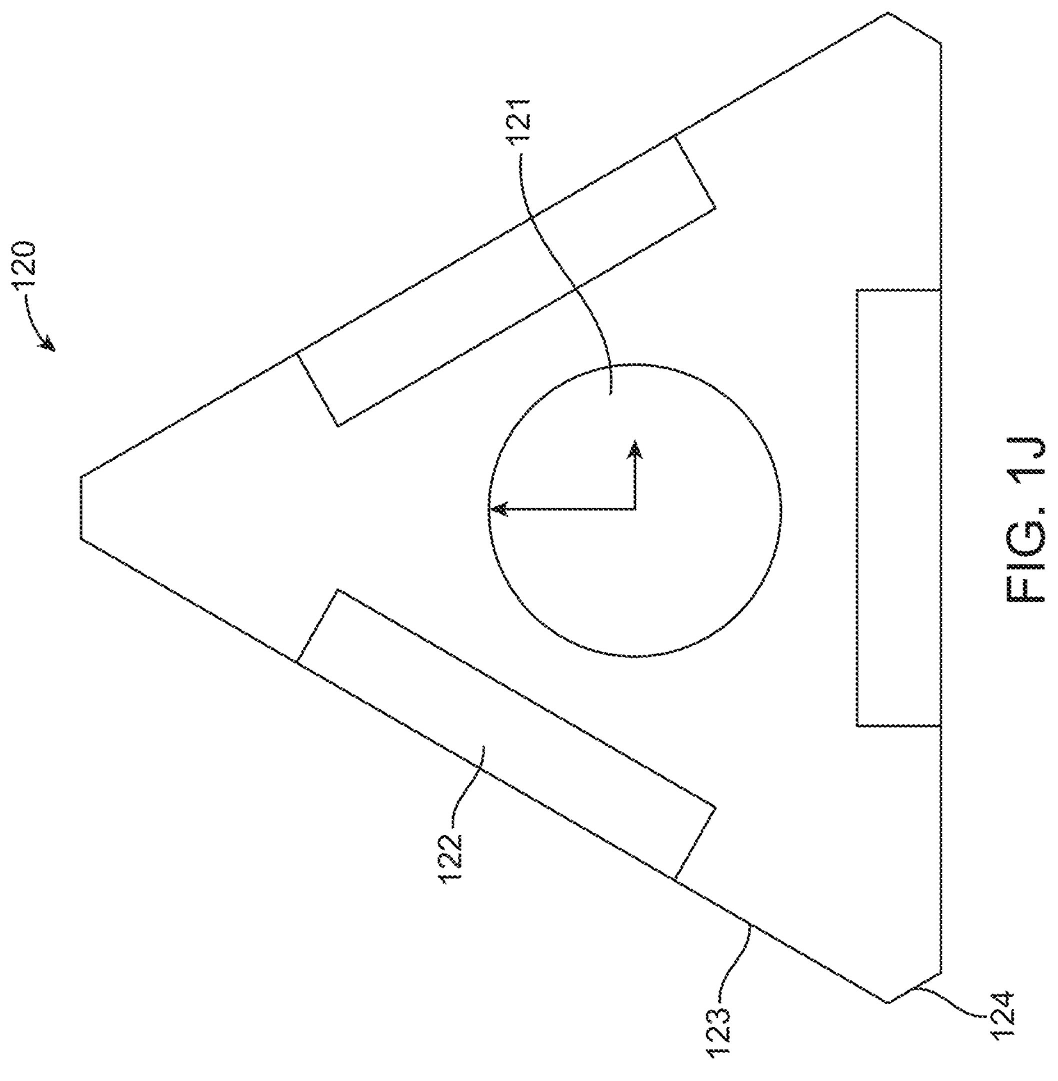

FIGS. 1H-J illustrate another embodiment of an implant structure 120 having a central lumen 121 and a side pocket 122 on each face 123 of the implant structure 120. The side pocket 122 can be a depression, cavity, groove or slot centered on the face 123 having a width, length and depth. In some embodiments, the side pocket 122 is relatively shallow so that it does not extend to the central lumen 121. In some embodiments, each apex 124 can be beveled or rounded. In some embodiments, the distal end 125 of the implant structure 120 can be tapered to facilitate implantation into the bone. In some embodiments, the implant structure 120 illustrated in FIGS. 1H-J has a relative bending strength of about 0.77 and a relative shear strength of about 0.72. In some embodiments, to load the implant structure 120 with bone graft materials, the bone graft material is applied to the side pockets 122 before implantation. In other embodiments, the bone graft material is applied during implantation, as further described in U.S. Patent Application 61/609,043 titled Tissue Dilator and Protector, which is hereby incorporated by reference in its entirety and can be applied to the other implants.

In some embodiments, the side pocket 122 can have a width (W4) that is about 0.5 of width (W5) of the face 123 of the implant structure 120. In some embodiments, the side pocket 122 can have a width that is greater than about 0.5 of the width of the face 123 of the implant structure 120. In some embodiments, the side pocket 122 can have a width that is less than about 0.5 of the width of the face 123 of the implant structure 120. In some embodiments, the side pocket 122 can have a width that is between about 0.2 to about 0.8 of the width of the face 123 of the implant structure 120. In some embodiments, the side pocket 122 can have a length (L4) that is about 0.75 the length (L5) of the face 123. In some embodiments, the side pocket 122 can have a length that is less than about 0.75 the length of the face 123. In some embodiments, the side pocket 122 can have a length that is greater than about 0.75 the length of the face 123. In some embodiments, the side pocket 122 can have a length that is between about 0.5 to 0.9 of the length of the face 123. In some embodiments, the side pocket 122 can have a depth between about 0.2 mm and 5 mm, or between about 0.2 mm and 2 mm, or between about 0.2 and 1 mm. In some embodiments, the side pocket 122 can have a depth between about 0.25 mm, 0.5 mm, 0.75 mm, 1 mm or 2 mm. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1K:
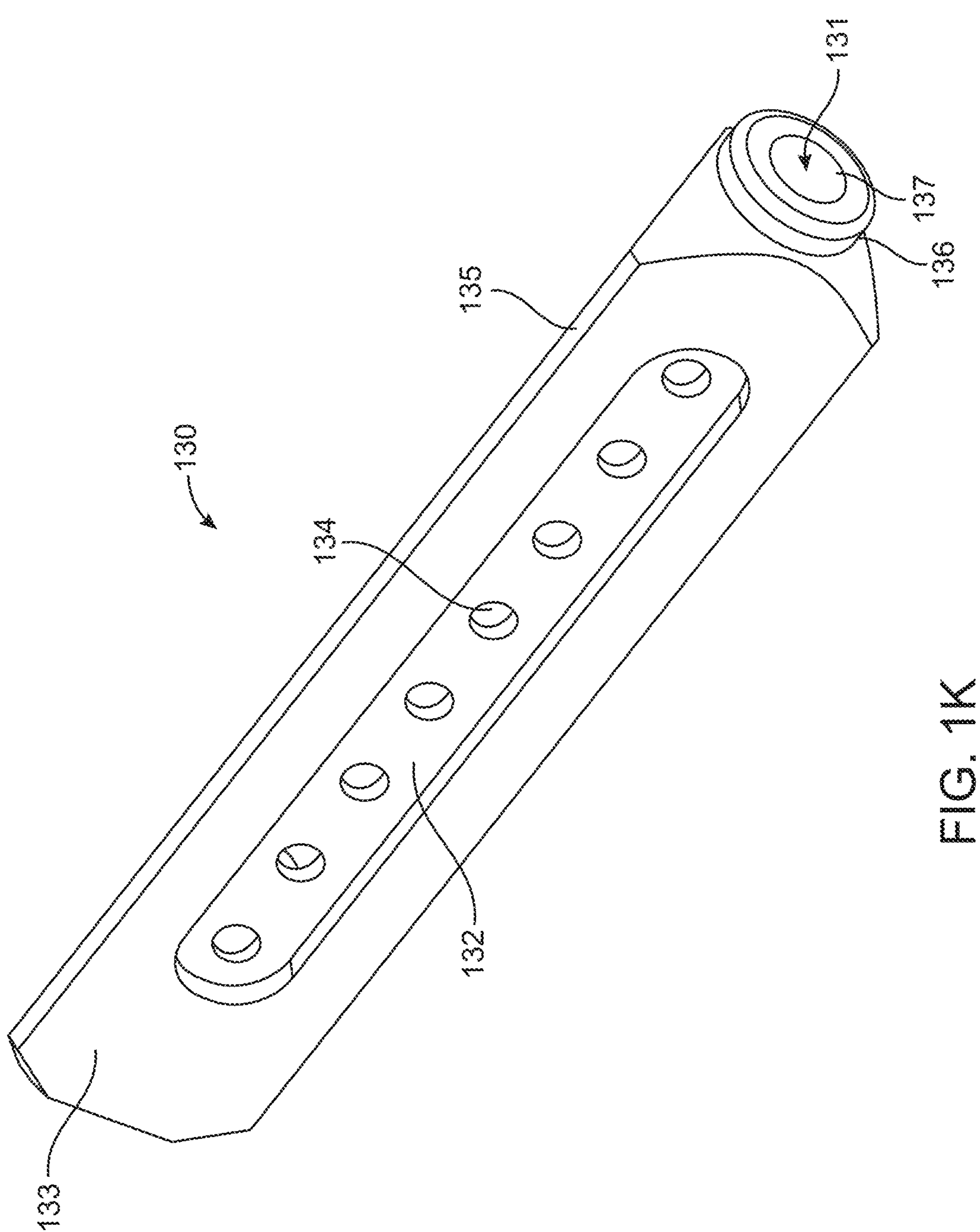
Figure 1L:
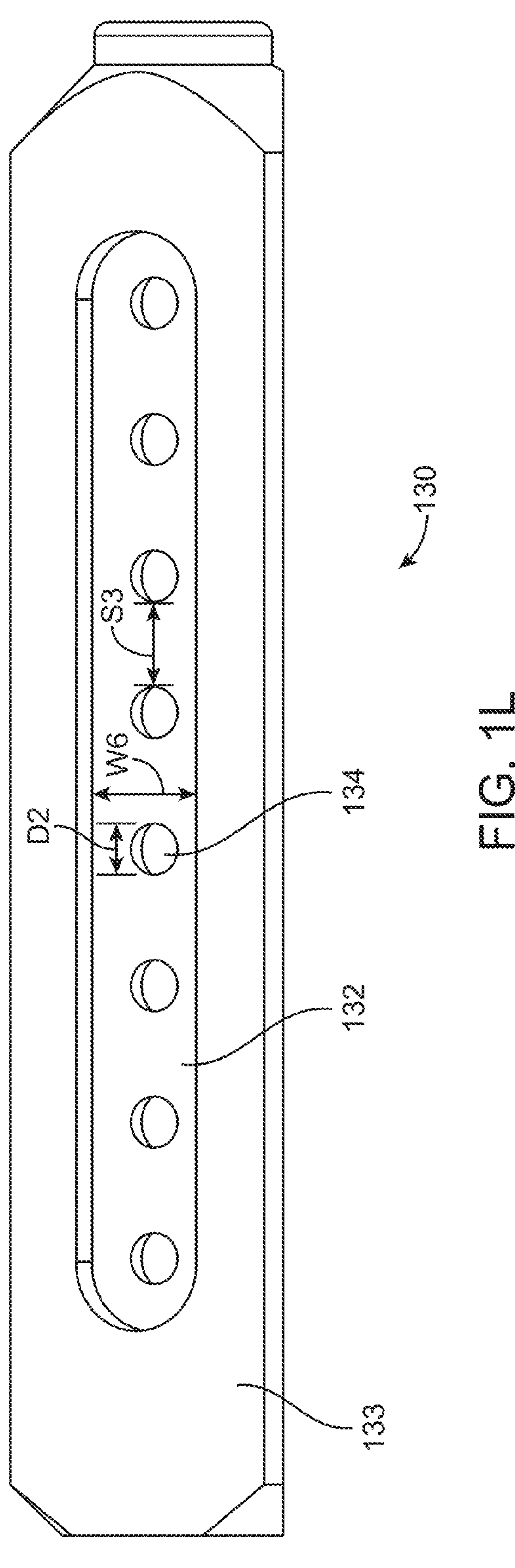
Figure 1M:
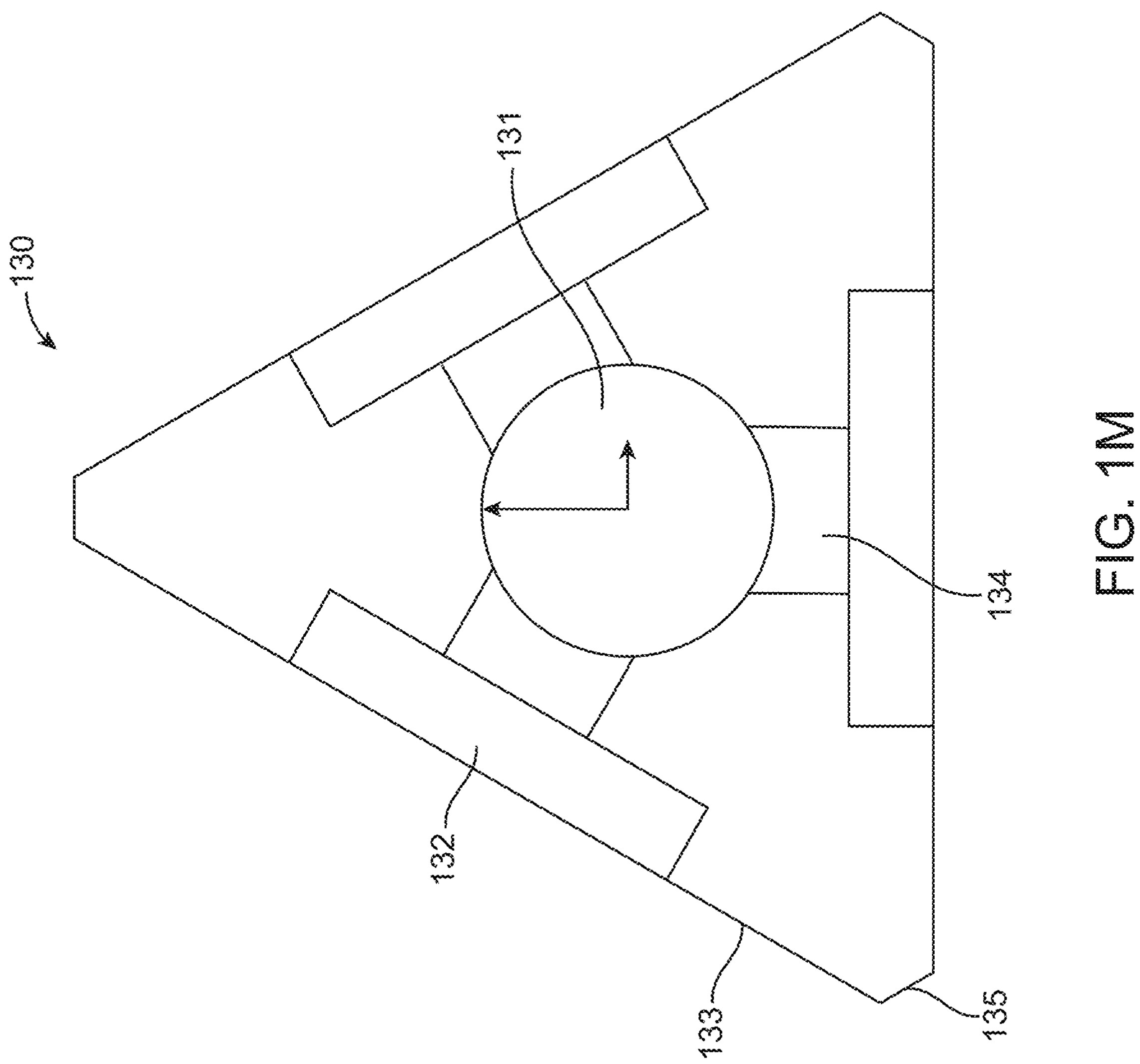

FIGS. 1K-M illustrate another embodiment of an implant structure 130 having a central lumen 131, a side pocket 132 on each face 133 of the implant structure 130, and a plurality of holes 134 located within the side pocket 132. The side pocket 132 in the embodiment illustrated in FIGS. 1K-M can be the same as or be similar to the side pocket 122 previously described above and illustrated in FIGS. 1H-J. Likewise, the holes 134 illustrated in FIGS. 1K-M can be the same as or be similar to the holes 102 previously described above and illustrated in FIGS. 1B-D. In some embodiments, as illustrated in FIGS. 1K-M, the holes 134 have a diameter that is less than the diameter of the central lumen 131. In other embodiments, the holes 134 have a diameter than is equal to or greater than the diameter of the central lumen 131. In some embodiments, each apex 135 can be beveled or rounded. In some embodiments, the distal end 136 of the implant structure 130 can be tapered to facilitate implantation into the bone. In some embodiments, the implant structure 130 illustrated in FIGS. 1K-M has a relative bending strength of about 0.74 and a relative shear strength of about 0.62. In some embodiments, to load the implant structure 130 with bone graft materials, the bone graft material is injected and/or applied to the side pockets 132 and holes 134 before implantation. In other embodiments, the bone graft materials can be injected into the central lumen 131, which can have a distal opening 137 that is blocked off or plugged so that the bone graft materials fill the central lumen 131 and exit out the holes 134 which are in fluid communication with the central lumen 131. As the bone graft materials exit the holes 134, the bone graft material can coat and fill both the holes 134 and the side pocket 132. This injection process can be done before implantation, during implantation, or after implantation.

In some embodiments, the side pocket 132 shown in FIGS. 1K-M has the same or similar dimensions as the side pocket 122 shown in FIGS. 1H-J and described above. In some embodiments, the holes 134 can have a diameter (D2) that is about 0.4 of the width (W6) of the side pocket 132. In some embodiments, the holes 134 can have a diameter that is greater than or less than about 0.4 times the width of the side pocket 132. In some embodiments, the holes 134 can be separated (S3) by about 1.5 times the diameter of the holes 134. In some embodiments, the holes 134 can be separated by greater than or less than about 1.5 times the diameter of the holes 134. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1N:
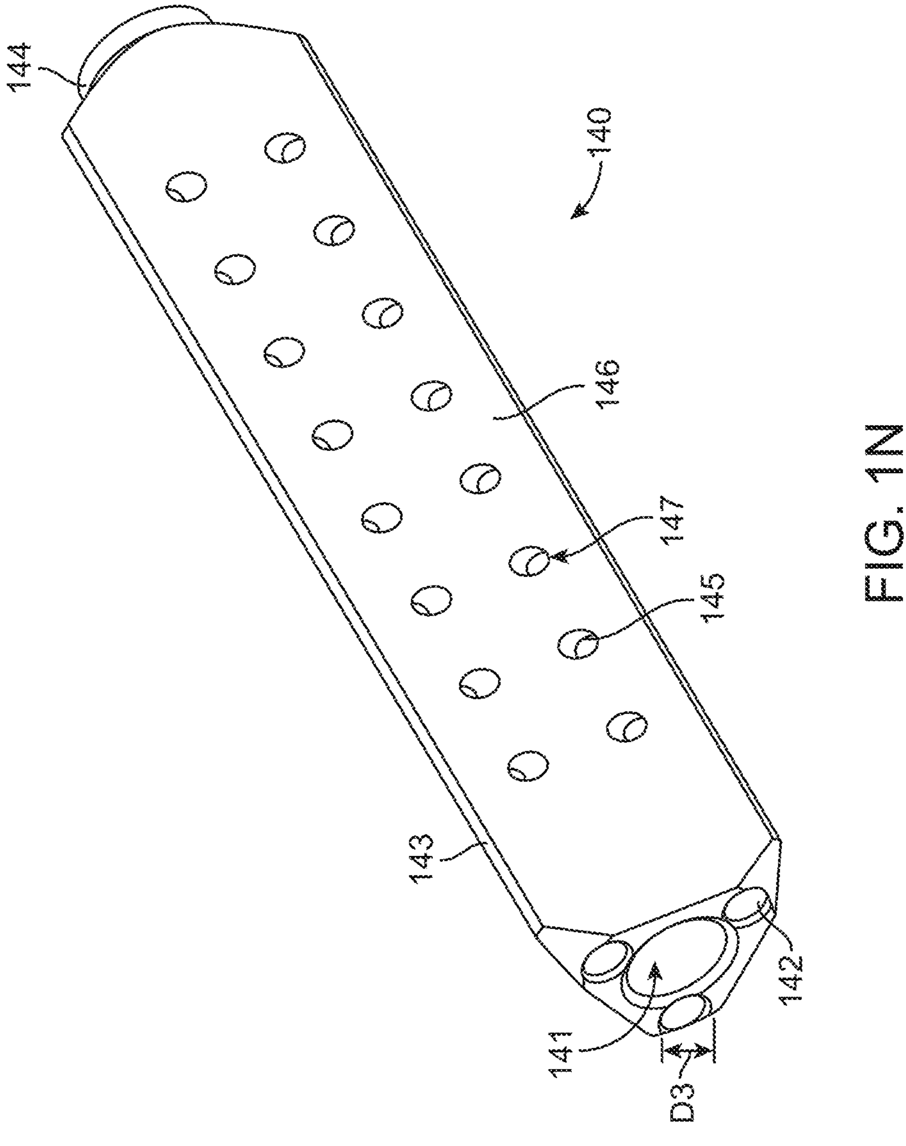
Figure 1O:
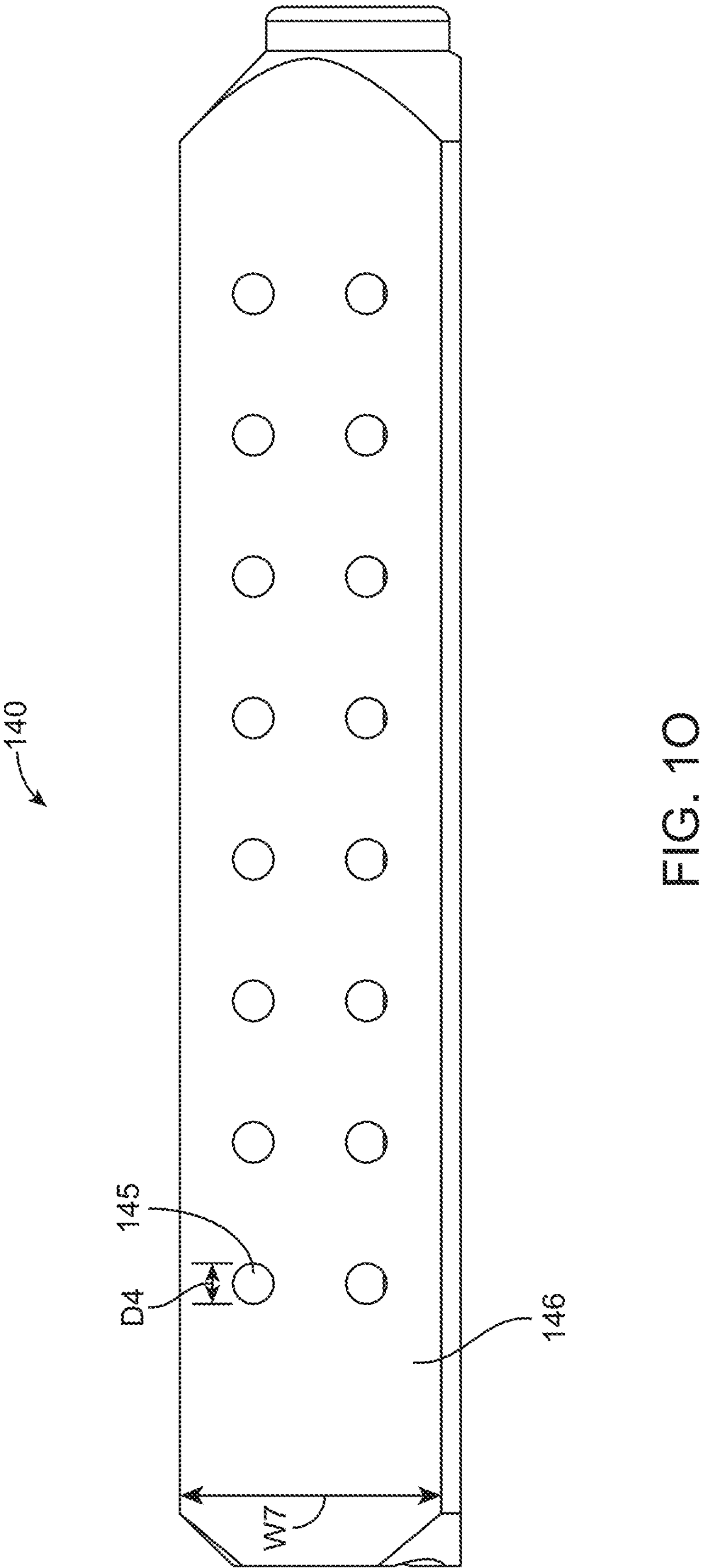
Figure 1P:
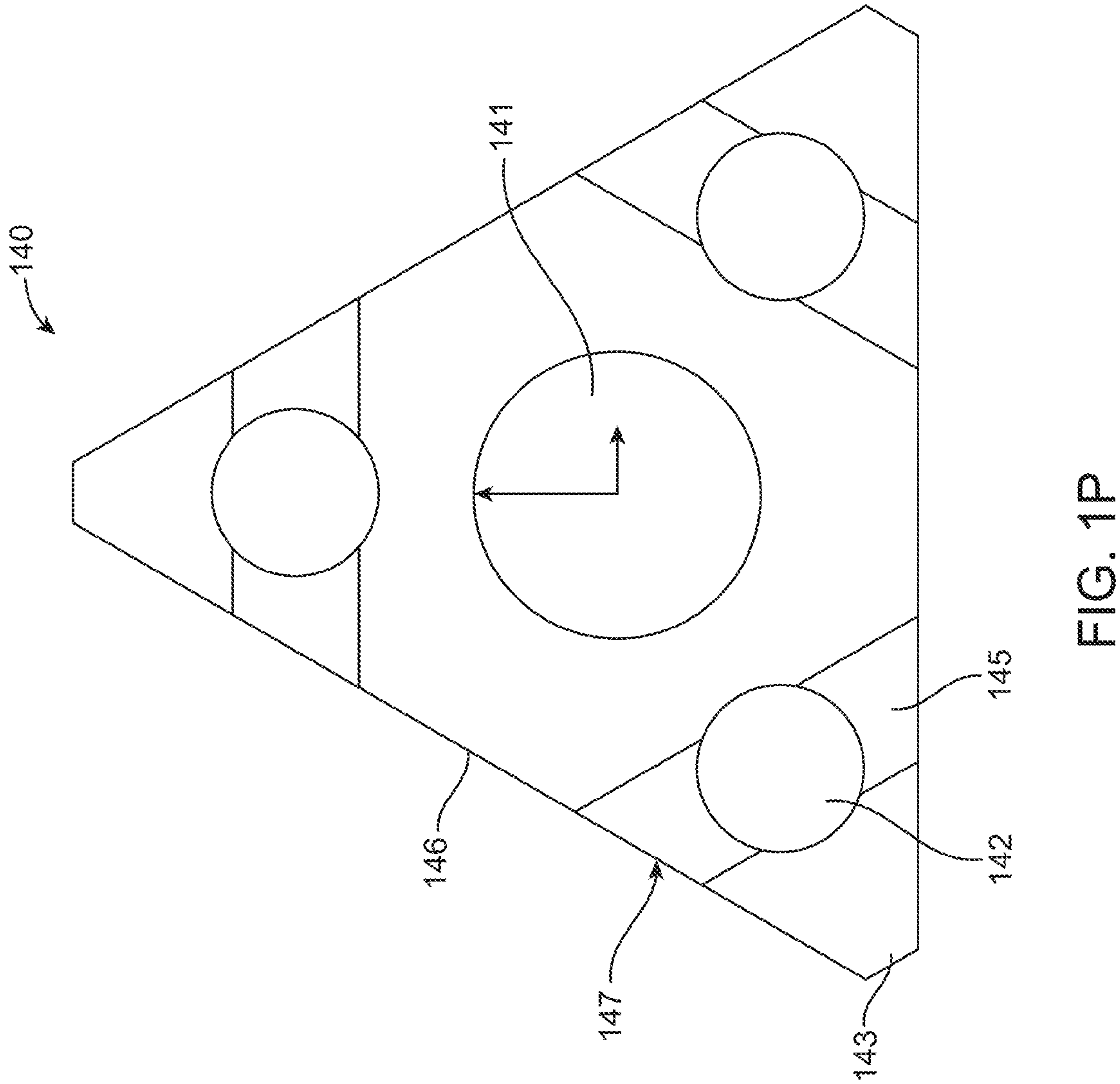

FIGS. 1N-P illustrate another embodiment of an implant structure 140 having a central lumen 141 and a plurality of peripheral lumens 142 surrounding the central lumen 141. The peripheral lumens 142 can be oriented longitudinally and can be located between the central lumen 141 and each apex 143. As illustrated, the implant structure 140 is triangular and has three apexes 143 and three peripheral lumens 142 that surround the central lumen 141. In some embodiments, both the central lumen 141 and the peripheral lumens 142 can extend throughout the longitudinal length of the implant structure 140. In other embodiments, the peripheral lumens 142 do not extend throughout the length of the implant structure 140, and instead, the peripheral lumens 142 terminate prior to the distal end 144 of the implant structure 140. In addition, a plurality of side holes 145 can be included in the implant structure 140. Each peripheral lumen 142 can be intersected by a plurality of side holes 145, where each side hole 145 extends between two faces 146 of the implant structure with a side hole opening 147 on each of the two faces 146. The side holes 145 can extend transversely through the implant structure 140 at an angle of about 60 degrees from the surfaces of the faces 146. In some embodiments, each apex 143 can be beveled or rounded. In some embodiments, the distal end 144 of the implant structure 140 can be tapered to facilitate implantation into the bone. In some embodiments, the implant structure 140 illustrated in FIGS. 1N-P has a relative bending strength of about 0.63 and a relative shear strength of about 0.66. In some embodiments, to load the implant structure 140 with bone graft materials, the bone graft material is injected into the peripheral lumens 142, where the bone graft material fills up the peripheral lumens and exits the side holes 145. Injection of the bone graft material can take place before, during, or after implantation. In some embodiments where the peripheral lumens 142 extend completely through the implant structure 140, the distal ends of the peripheral lumens 142 can be blocked or plugged before injection of the bone graft material.

In some embodiments, the peripheral lumens 142 have a diameter (D3) of about 0.2 times the width (W7) of the faces 146 of the implant structure. In some embodiments, the peripheral lumens 142 have a diameter greater than or less than about 0.2 times the width of the faces 146 of the implant structure. In some embodiments, the peripheral lumens 142 can have a smaller diameter than the central lumen 141. In other embodiments, the peripheral lumens 142 can have an equal or larger diameter than the central lumen 141. In some embodiments, the side holes 145 have a diameter (D4) equal or substantially equal to the diameter of the peripheral lumens 142. In other embodiments, the side holes 145 have a diameter less than or greater than the diameters of the peripheral lumens 142. In some embodiments, the relative bending strength can be at least about 0.5, 0.6, 0.7, 0.8 or 0.9. In some embodiments, the relative bending strength can be between about 0.5 to 0.9. In some embodiments, the relative shear strength can be at least about 0.5, 0.6, 0.7, 0.8 or 0.9. In some embodiments, the relative shear strength can be between about 0.5 to 0.9.

Figure 1Q:
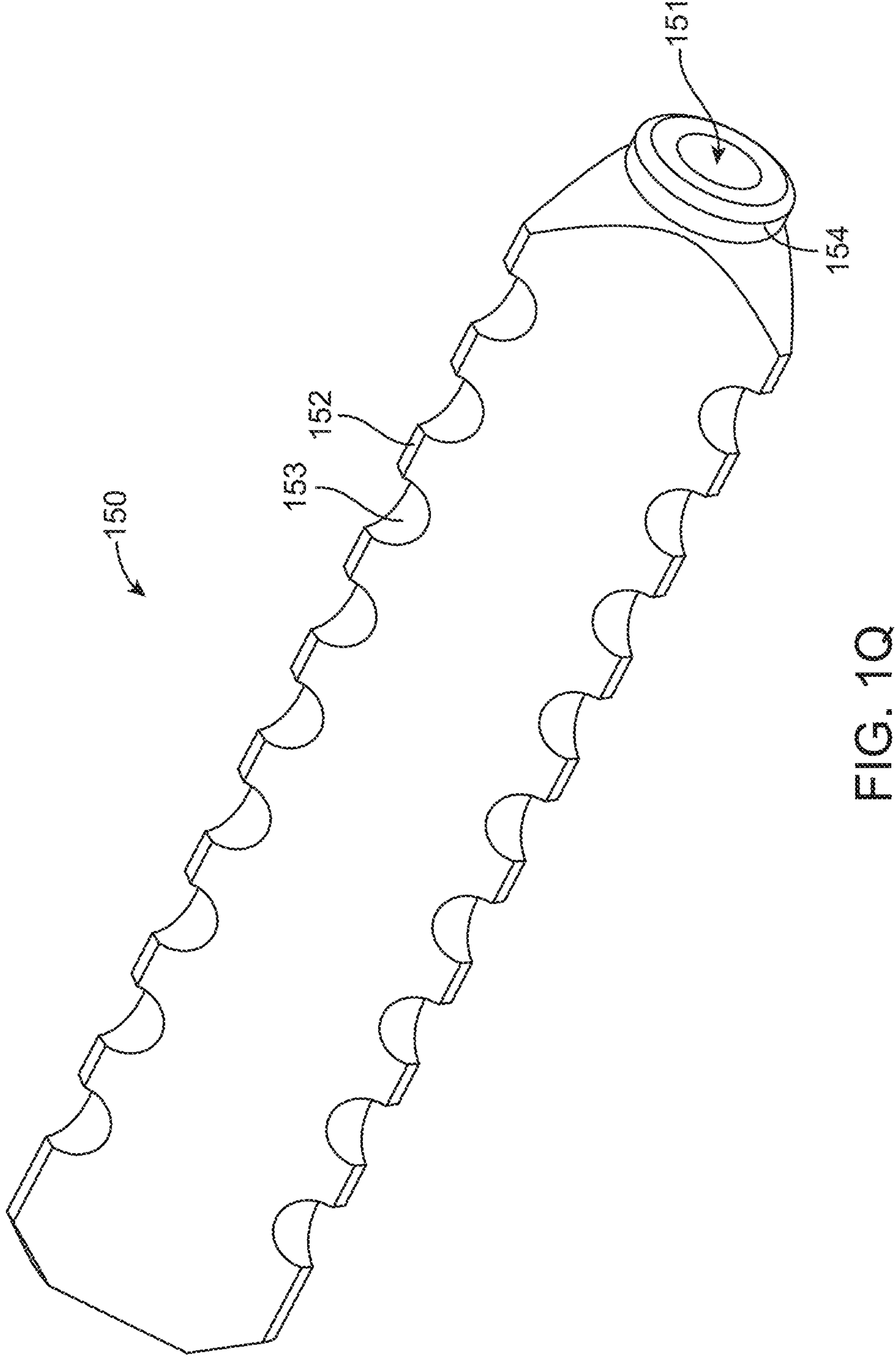
Figure 1R:
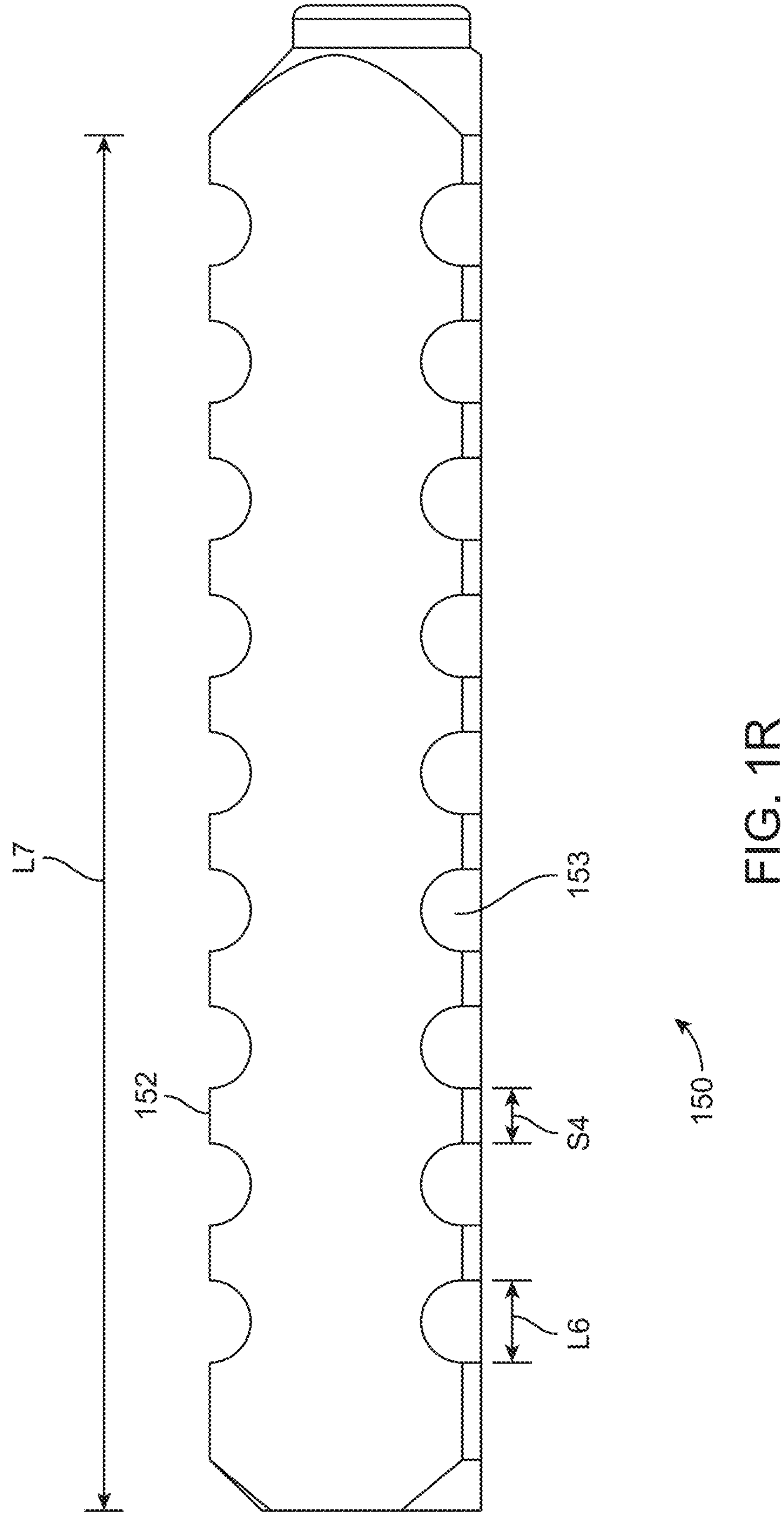
Figure 1S:
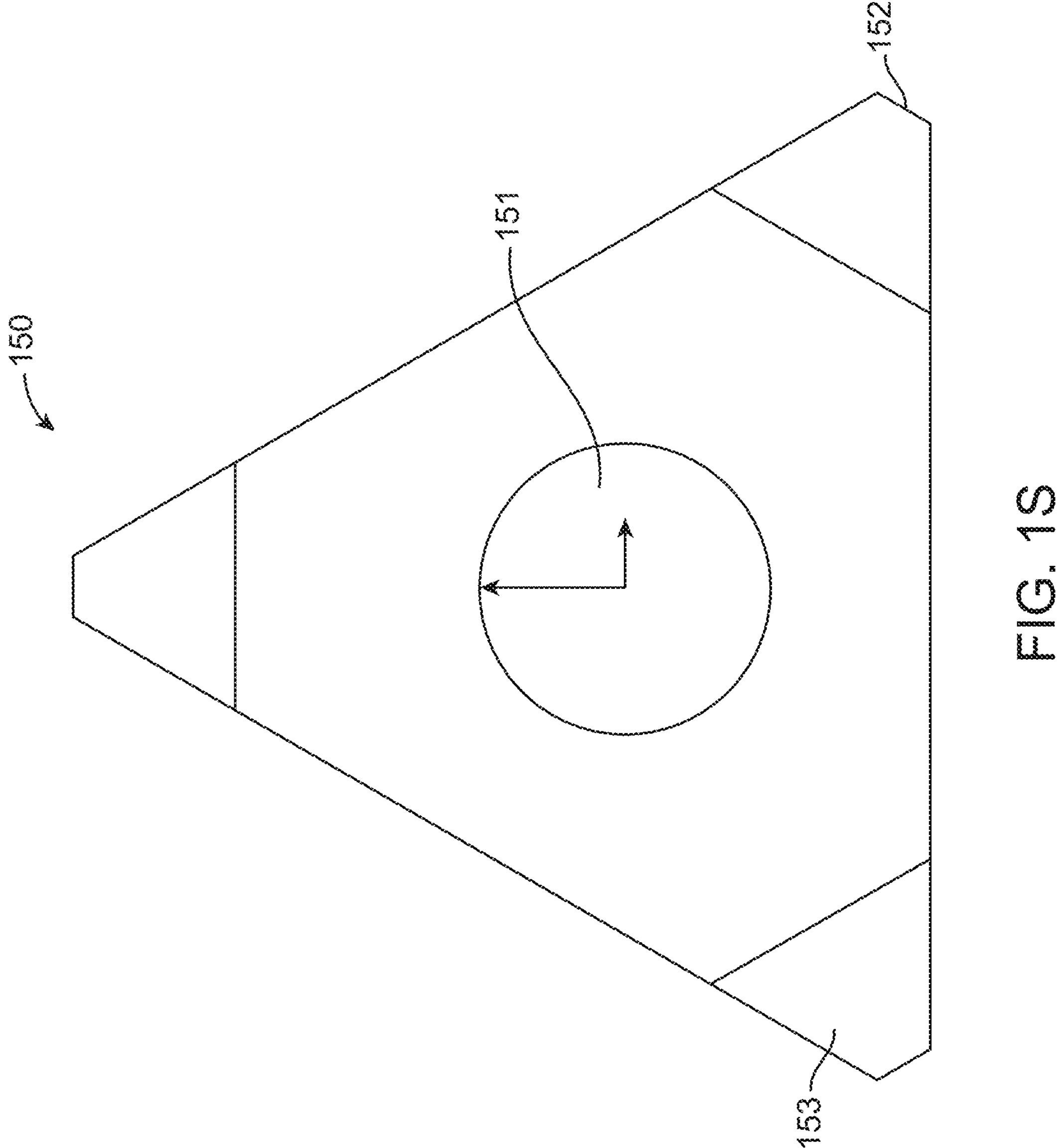

FIGS. 1Q-S illustrate another embodiment of an implant structure 150 having a central lumen 151. Each apex 152 can be beveled or rounded and can have a plurality of pockets or cavities 153 located at discrete points along the length of the apex 152. These pockets 153 extend from the apex 152 and towards the central lumen 151, but do not reach the central lumen 151. In some embodiments, the pockets 153 have a curved cutout shape, which can correspond in shape to a portion of a cylinder. In some embodiments, the distal end 154 of the implant structure 140 can be tapered to facilitate implantation into the bone. In some embodiments, the implant structure 150 illustrated in FIGS. 1Q-S has a relative bending strength of about 0.89 and a relative shear strength of about 0.86. In some embodiments, to load the implant structure 150 with bone graft materials, the bone graft material is applied externally to the implant structure 150 either before or during implantation. In addition to receiving the bone graft materials, the pockets 153 also function to eliminate or reduce a corner haloing effect.

In some embodiments, the pockets 153 can have a length (L6) or diameter of about 0.06 of the length (L7) of the apex 152. In some embodiments, the pockets 153 can have a length or diameter greater than or less than about 0.06 of the length of the apex 152. In some embodiments, the pockets 153 can be separated (S4) from adjacent pockets 153 by about ⅔ of the pocket length or diameter. In some embodiments, the pockets 153 can be separated from adjacent pockets 153 by greater than or less than about ⅔ of the hole diameter. In some embodiments, the relative bending strength can be at least about 0.5, 0.6, 0.7, 0.8 or 0.9. In some embodiments, the relative bending strength can be between about 0.5 to 0.95. In some embodiments, the relative shear strength can be at least about 0.5, 0.6, 0.7, 0.8 or 0.9. In some embodiments, the relative shear strength can be between about 0.5 to 0.95.

Figure 1T:
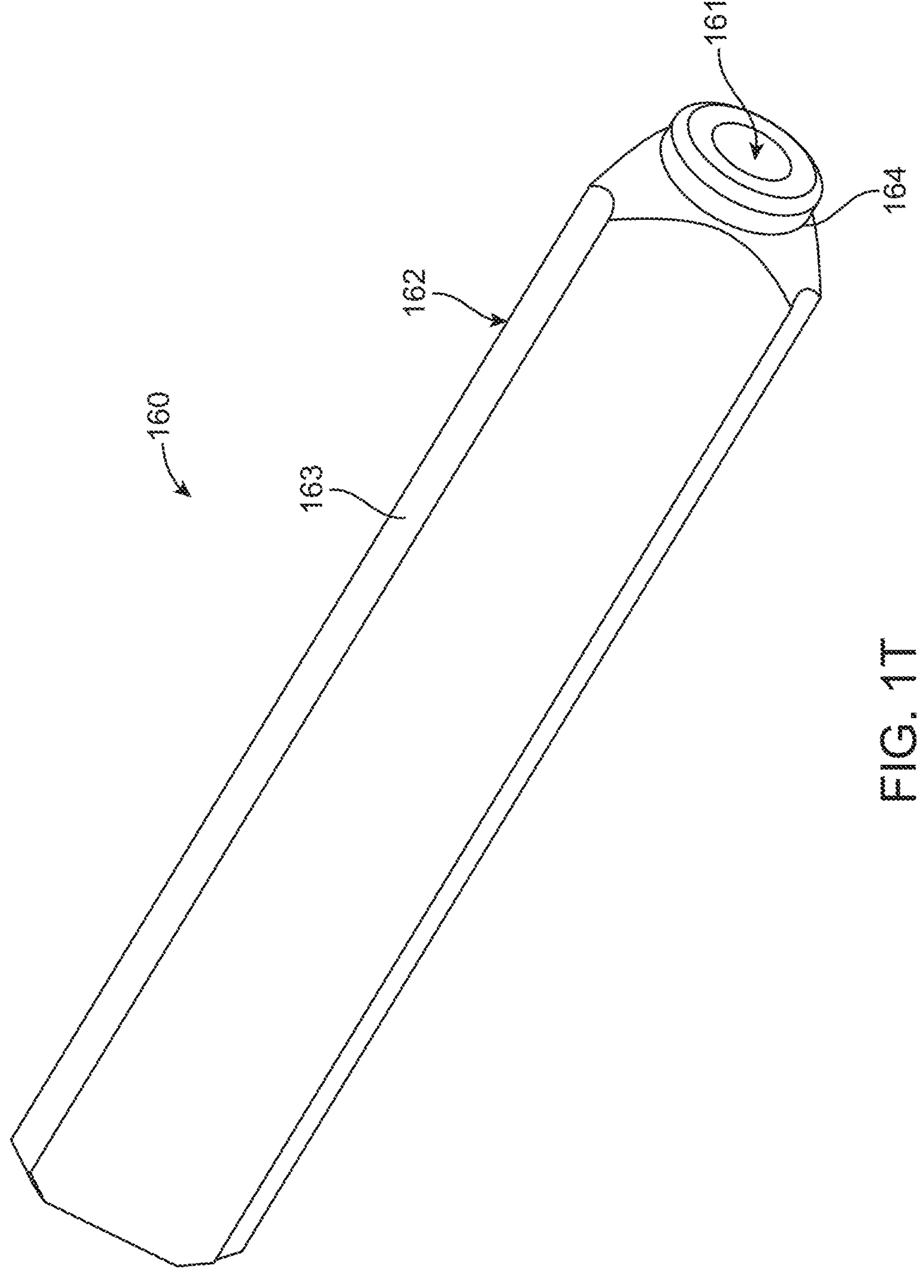
Figure 1U:
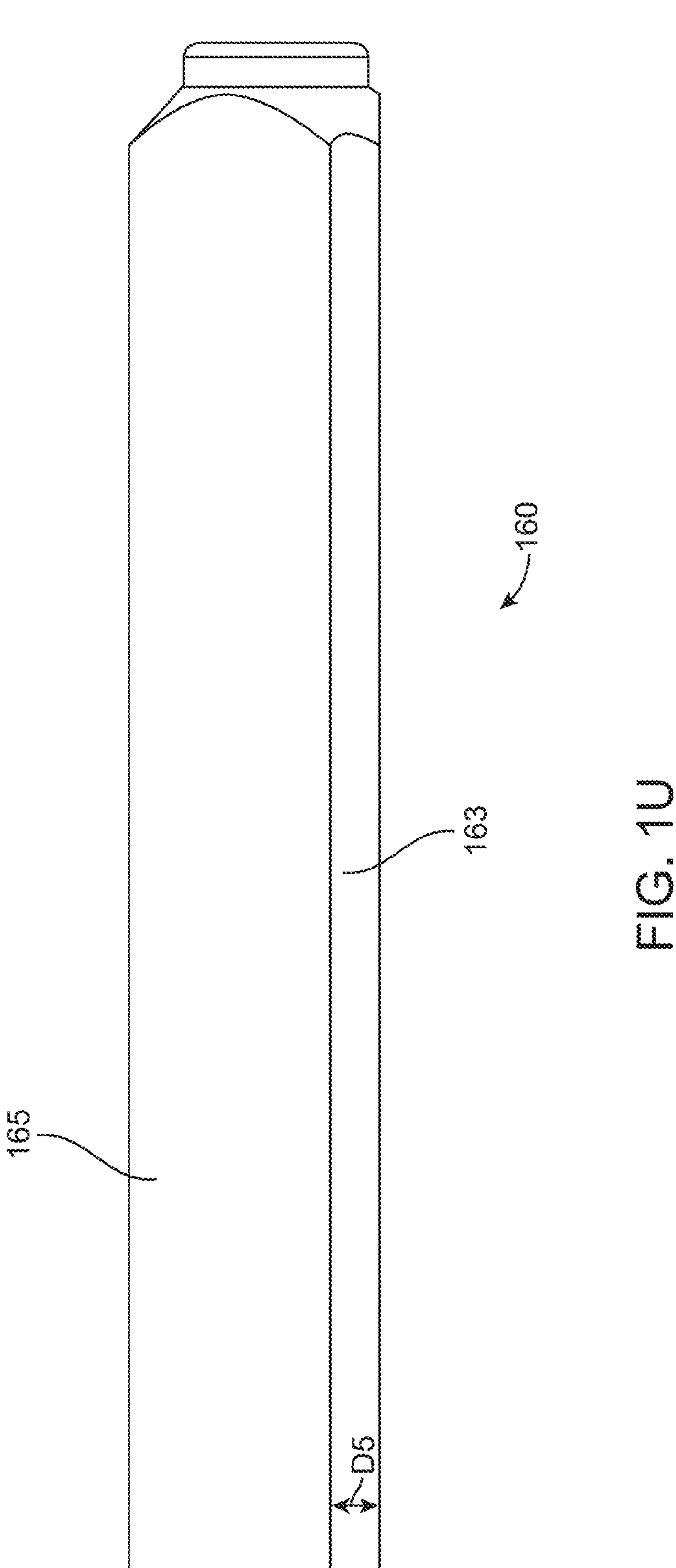
Figure 1V:
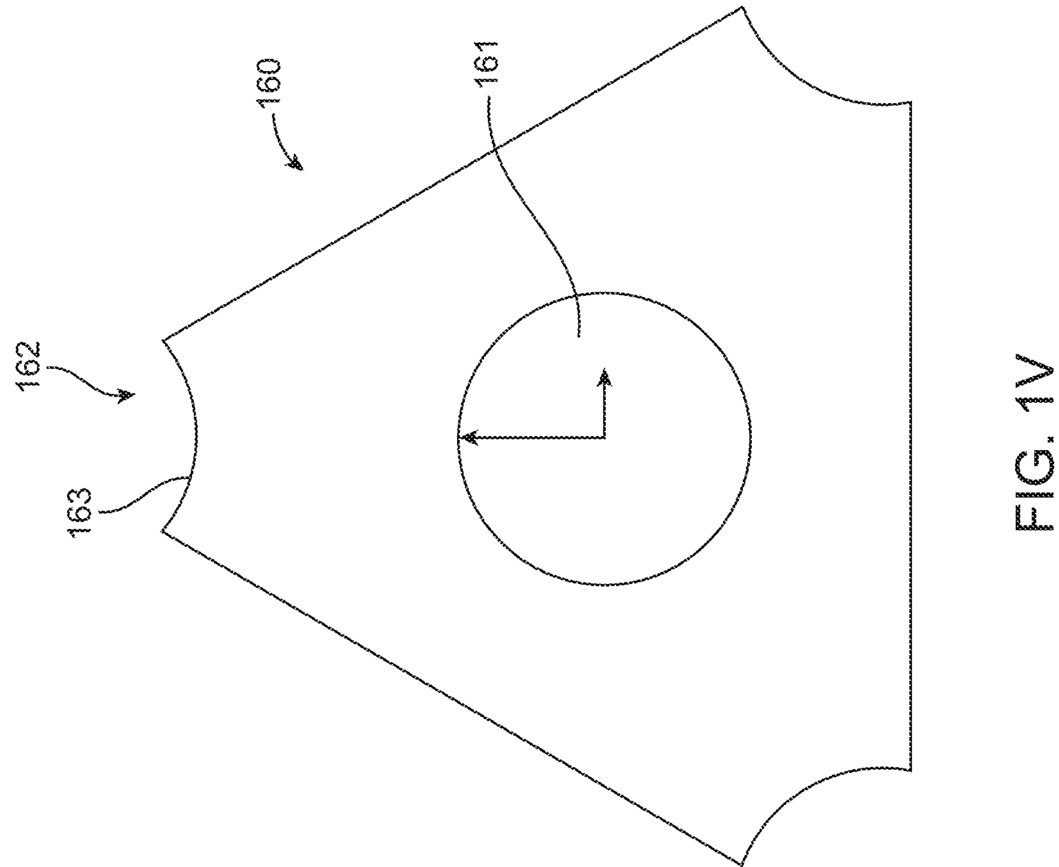

FIGS. 1T-V illustrate another embodiment of an implant structure 160 having a central lumen 161. Each apex 162 has a groove 163 that extends along the length of the apex 162. In some embodiments, the distal end 164 of the implant structure 160 can be tapered to facilitate implantation into the bone. In some embodiments, the implant structure 160 illustrated in FIGS. 1T-V has a relative bending strength of about 0.87 and a relative shear strength of about 0.88. In some embodiments, to load the implant structure 160 with bone graft materials, the bone graft material is applied externally to the implant structure 160 either before or during implantation. In addition to receiving the bone graft materials, the grooves 163 also function to eliminate or reduce a corner haloing effect.

In some embodiments, the grooves 163 can be circular shaped cutouts running along the apex 162 having a diameter (D5) of about 0.25 of the width of the face 165 and an arc length of about 0.28 of the width of the face 165. In some embodiments, the grooves 163 can have a diameter of greater or less than about 0.25 of the width of the face 165. In some embodiments, the grooves 163 can have an arc length of greater than or less than about 0.28 of the width of the face 165.

Figures 5, 6:
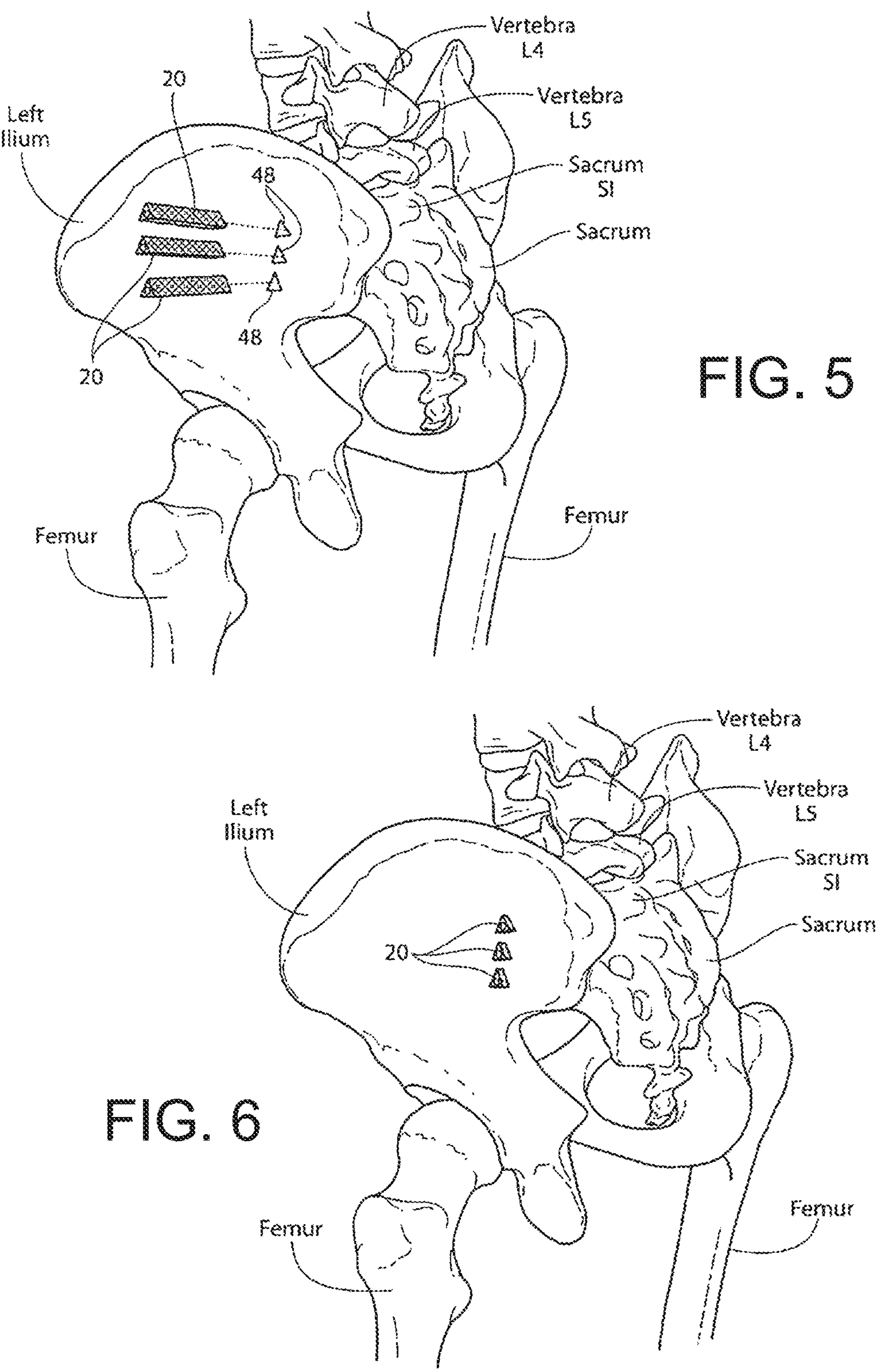
Figure 7A:
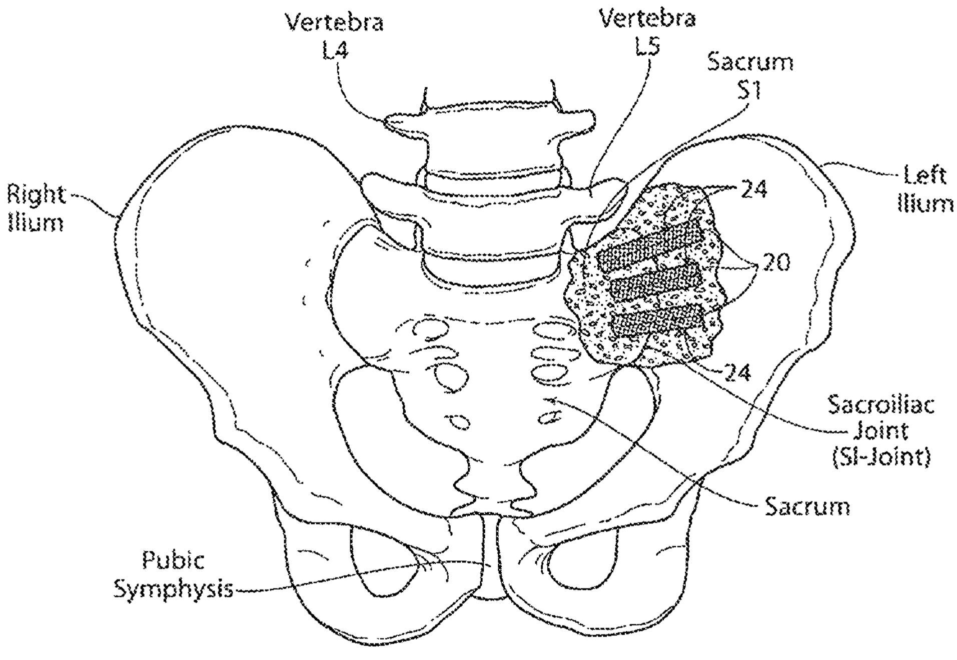

In one embodiment of a lateral approach (see FIGS. 5, 6, and 7A/B), one or more implant structures 20 are introduced laterally through the ilium, the SI-Joint, and into the sacrum. This path and resulting placement of the implant structures 20 are best shown in FIGS. 6 and 7A/B. In the illustrated embodiment, three implant structures 20 are placed in this manner. Also in the illustrated embodiment, the implant structures 20 are rectilinear in cross section and triangular in this case, but it should be appreciated that implant structures 20 of other cross sections can be used. In addition, any of the implant structures disclosed above can be used in the implantation procedures herein.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI Joint injection.

Figure 2D:
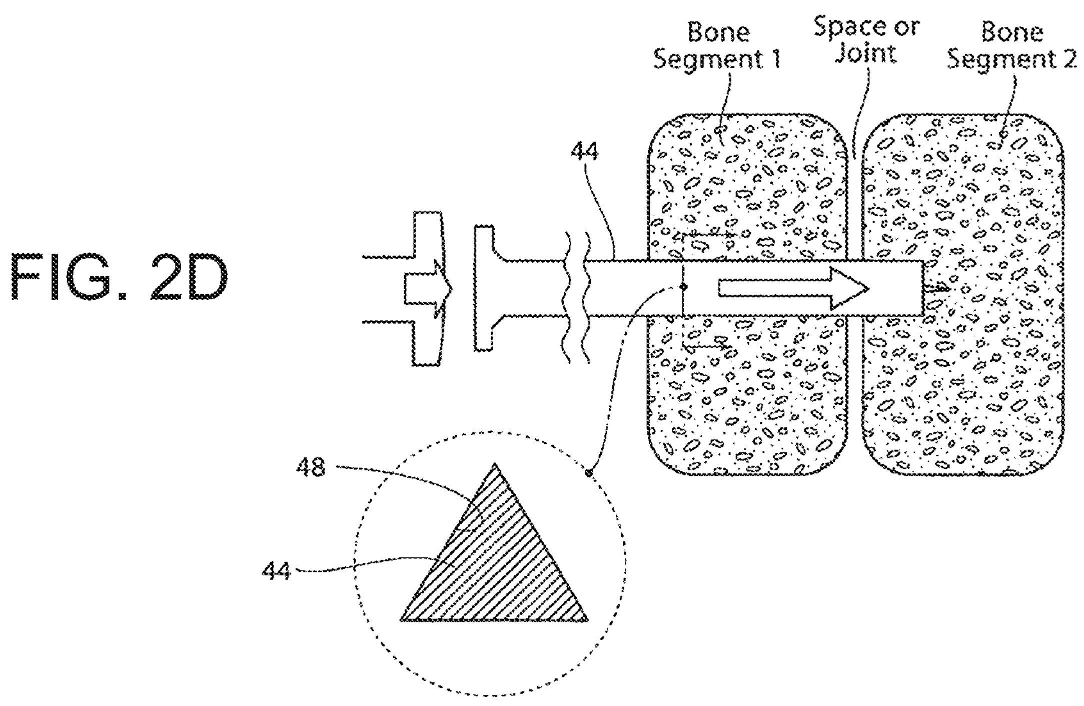
Figure 7B:
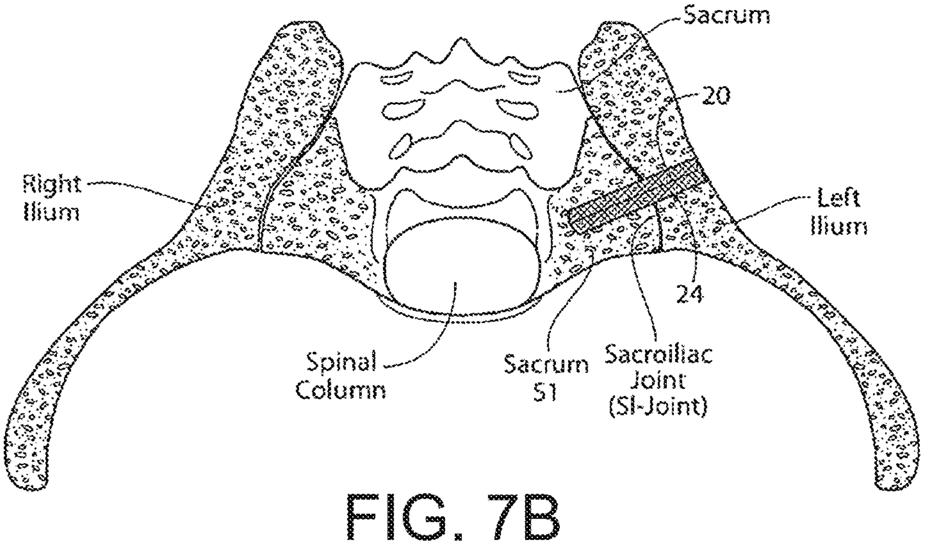
Figures 2A, 2B, 2C:
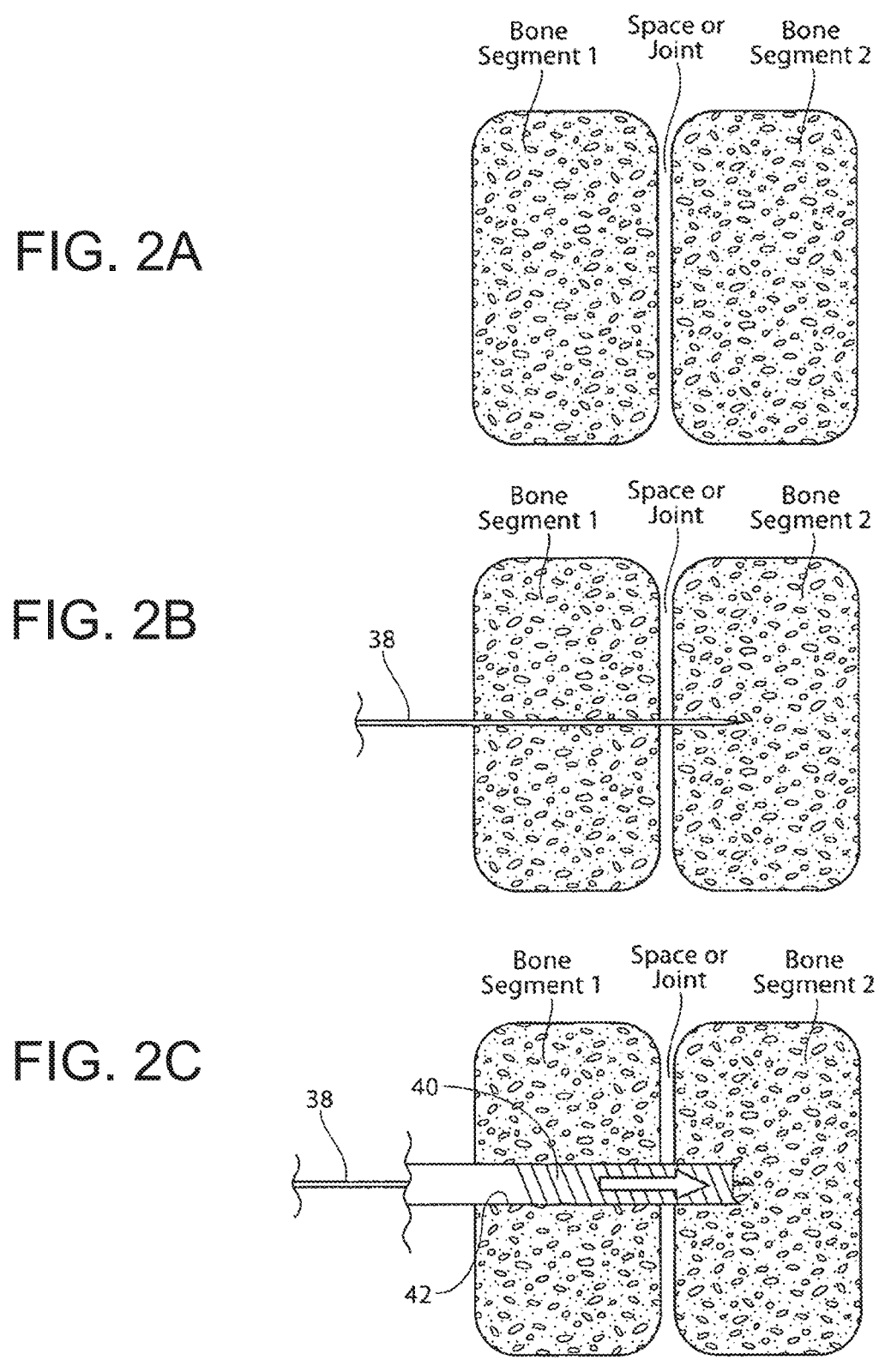

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate at a shallow angle anterior (e.g., 15 to 20 degrees off horizontal, as FIG. 7B shows). In a lateral view, the guide pin 38 should be posterior to the sacrum anterior wall. In the inlet view, the guide pin 38 should not violate the sacral foramina. This corresponds generally to the sequence shown diagrammatically in FIGS. 2A and 2B. A soft tissue protector (not shown) is desirably slipped over the guide pin 38 and firmly against the ilium before removing the guide pin sleeve (not shown).

Over the guide pin 38 (and through the soft tissue protector), the pilot bore 42 is drilled in the manner previously described, as is diagrammatically shown in FIG. 2C. The pilot bore 42 extends through the ilium, through the SI-Joint, and into the sacrum. The drill bit 40 is then removed.

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 2D. The triangular profile of the broached bore 48 is also shown in FIG. 5.

Figures 2E, 2F:
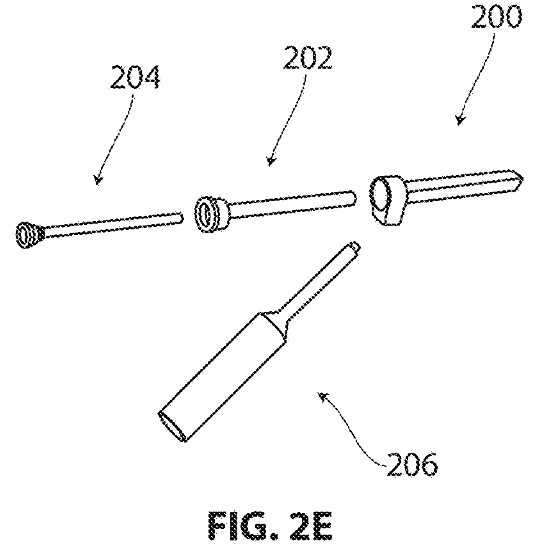
FIGS. 2E and 2F illustrate the assembly of a soft tissue protector system for placement over a guide wire.

FIGS. 2E and 2F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved. The soft tissue protector 200 can be any one of the soft tissue protectors or dilators or delivery sleeves disclosed herein. In some embodiments, an expandable dilator or delivery sleeve 200 as disclosed herein can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

As shown in FIGS. 5 and 6, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 7A and 7B). The guide pin 38 and soft tissue protector are withdrawn, leaving the implant structure 20 residing in the broached passageway, flush with the lateral wall of the ilium (see FIGS. 7A and 7B). In the illustrated embodiment, two additional implant structures 20 are implanted in this manner, as FIG. 6 best shows. In other embodiments, the proximal ends of the implant structures 20 are left proud of the lateral wall of the ilium, such that they extend 1, 2, 3 or 4 mm outside of the ilium. This ensures that the implants 1020 engage the hard cortical portion of the ilium rather than just the softer cancellous portion, through which they might migrate if there was no structural support from hard cortical bone. The hard cortical bone can also bear the loads or forces typically exerted on the bone by the implant 1020.

The implant structures 20 are sized according to the local anatomy. For the SI-Joint, representative implant structures 20 can range in size, depending upon the local anatomy, from about 35 mm to about 70 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Application No. 61/609,043, titled "TISSUE DILATOR AND PROTECTER" and filed Mar. 9, 2012, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium alloy provide immediate post-op SI Joint stability. A bony in-growth region 24 comprising a porous plasma spray coating with irregular surfaces supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

Figure 8A:
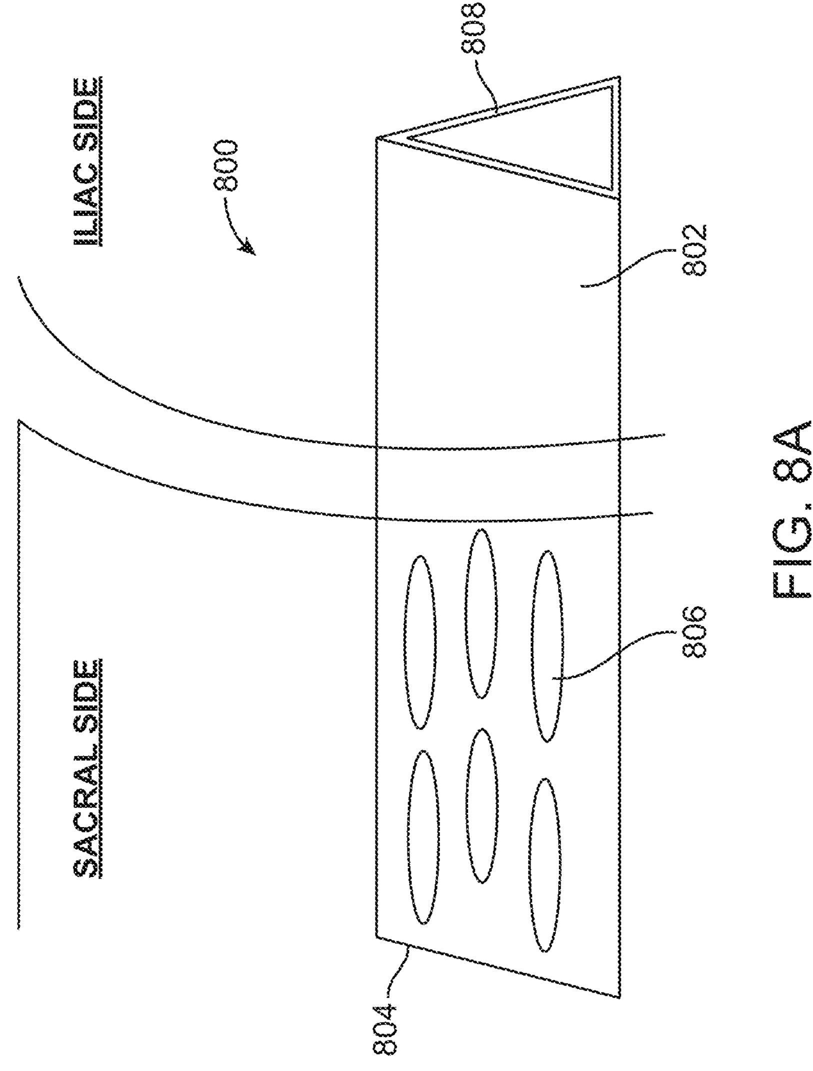
FIGS. 8A, 8B and 8C illustrate embodiments of implant structures with fenestrations.
Figure 8B:
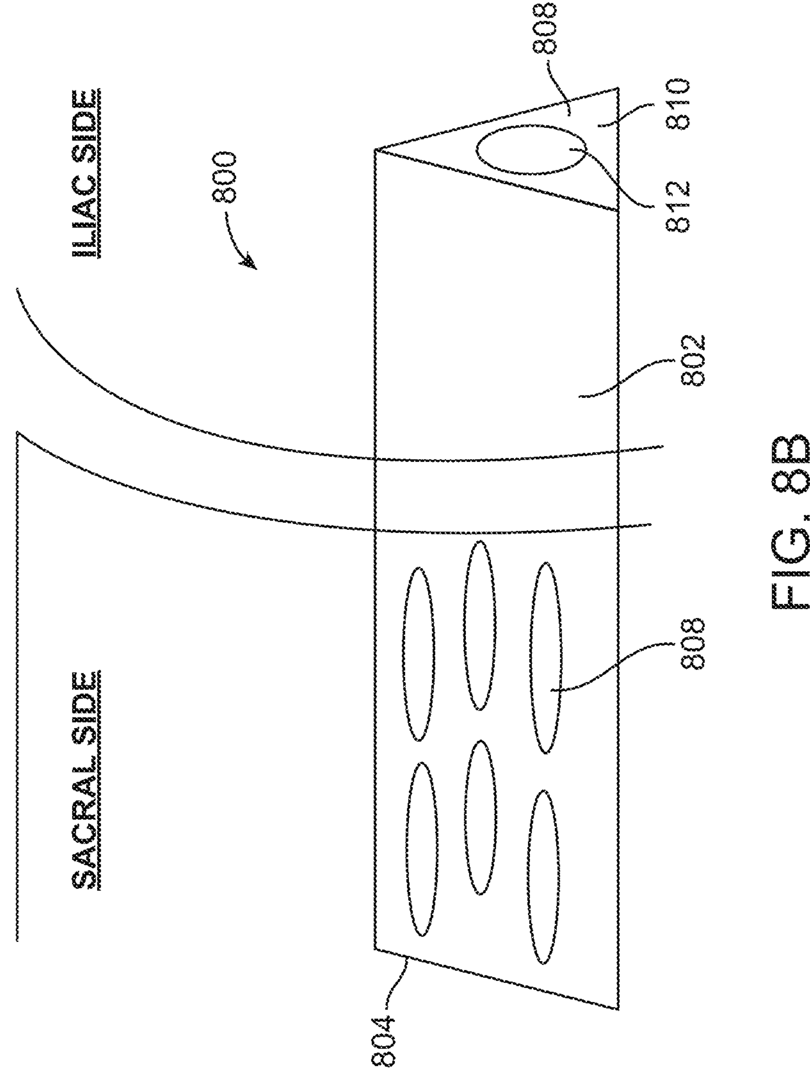
Figure 8C:
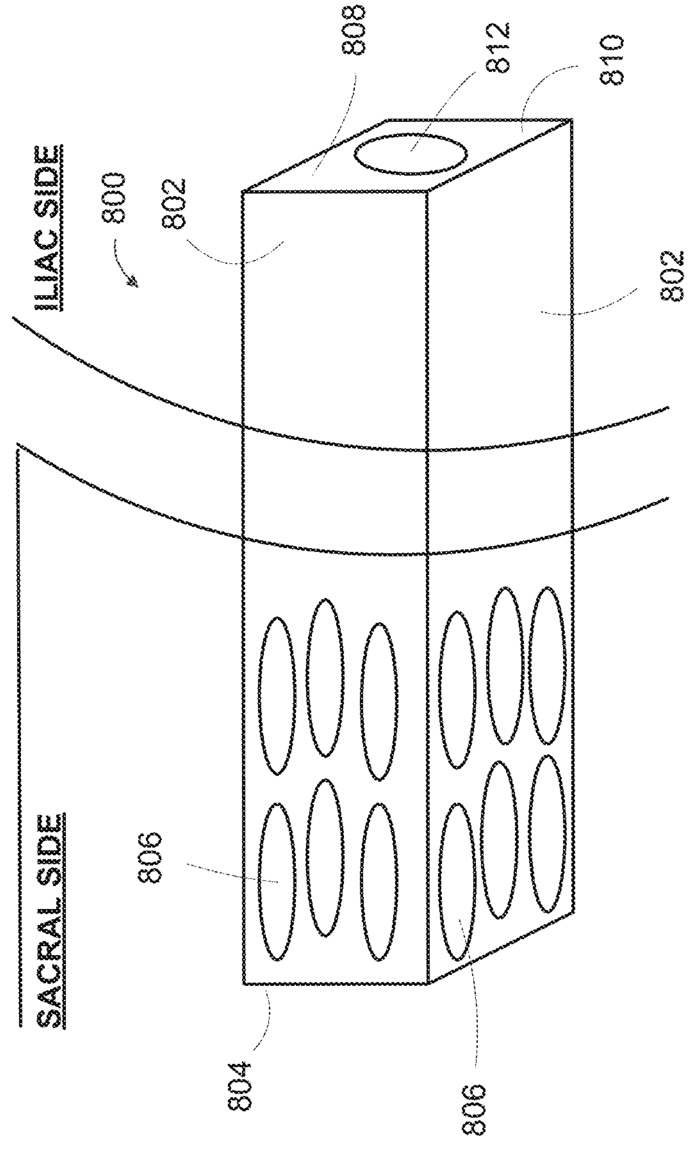

In some embodiments, as illustrated in FIGS. 8A and 8B, the implant structure 800 can have a rectilinear cross-sectional profile formed from a plurality of walls 802 having a thickness of approximately 2 to 3 mm, or 1 to 5 mm, or less than approximately 5, 4, 3, or 2 mm. In some embodiments, the rectilinear cross-sectional profile can be triangular, square or rectangular. In some embodiments, the implant structure 800 can have a substantially rectilinear cross-sectional profile formed by a plurality of apices that are joined together by a plurality of walls. The thin walled implant structure 800 can be advanced through the bone with little to no bony preparation. For example, in some embodiments, the implant structure 800 can be driven into the bone without first forming a bore that is shaped like the implant structure 800. In some embodiments, the distal end 804 of the implant structure 800 can be sharpened and/or have cutting edges like a chisel to facilitate the cutting of bone as the implant structure 800 is advanced. In some embodiments, an osteotome can be used to cut the bone before the implant structure 800 is inserted into the bone. For example, an osteotome as described in U.S. Provisional Application 61/800,966, titled "SYSTEMS AND METHODS FOR REMOVING AN IMPLANT" and filed on Mar. 15, 2013, which is herein incorporated by reference in its entirety for all purposes, can be adapted to pre-cut the bone to facilitate insertion of the implant structure 800 without forming a complete bore. In some embodiments, a bore can be formed as described above, and the implant structure 800 can then be inserted into the bore.

Figure 9A:
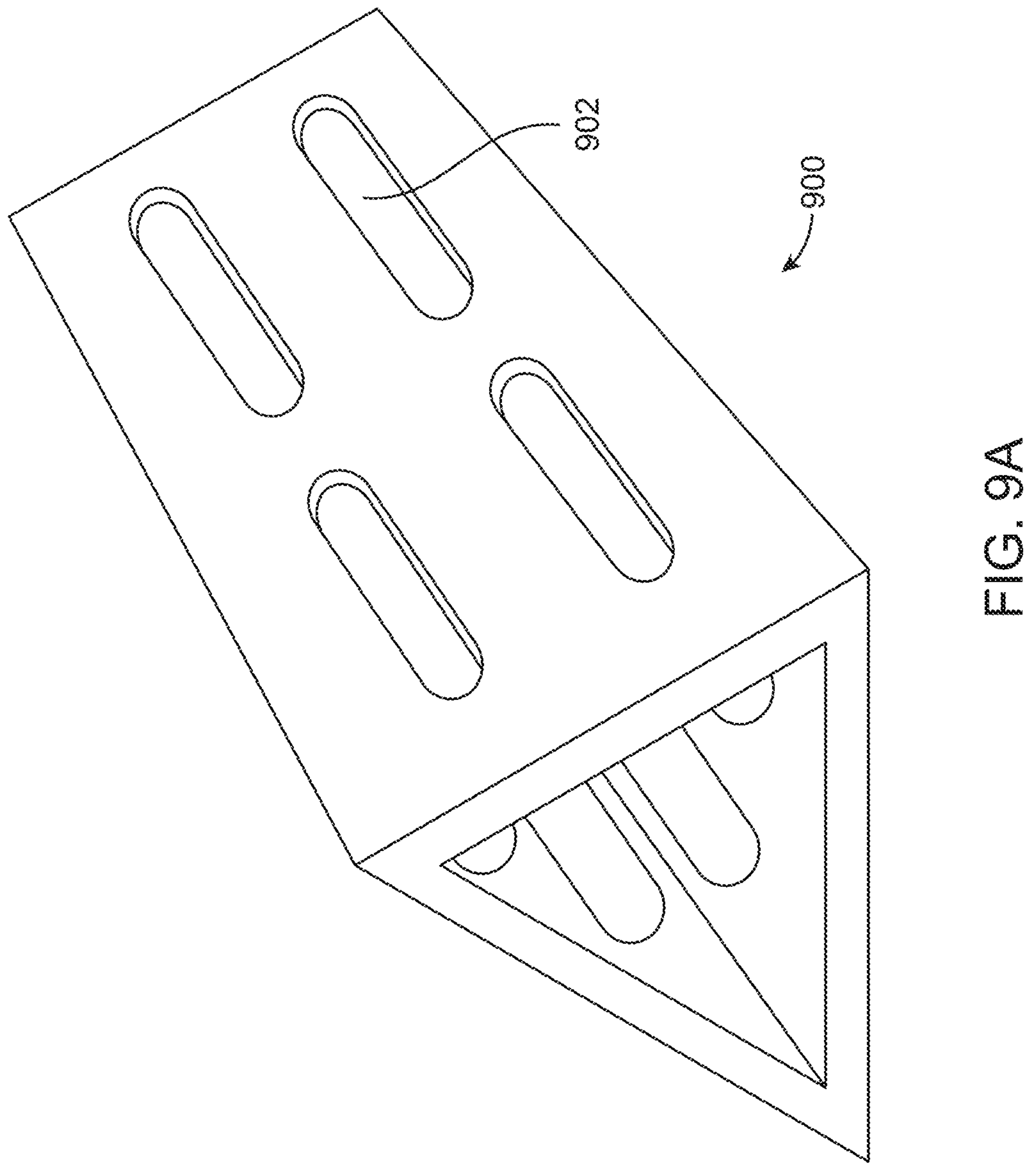
FIGS. 9A and 9B illustrate yet another embodiment of an implant structure with fenestrations.
Figure 9B:
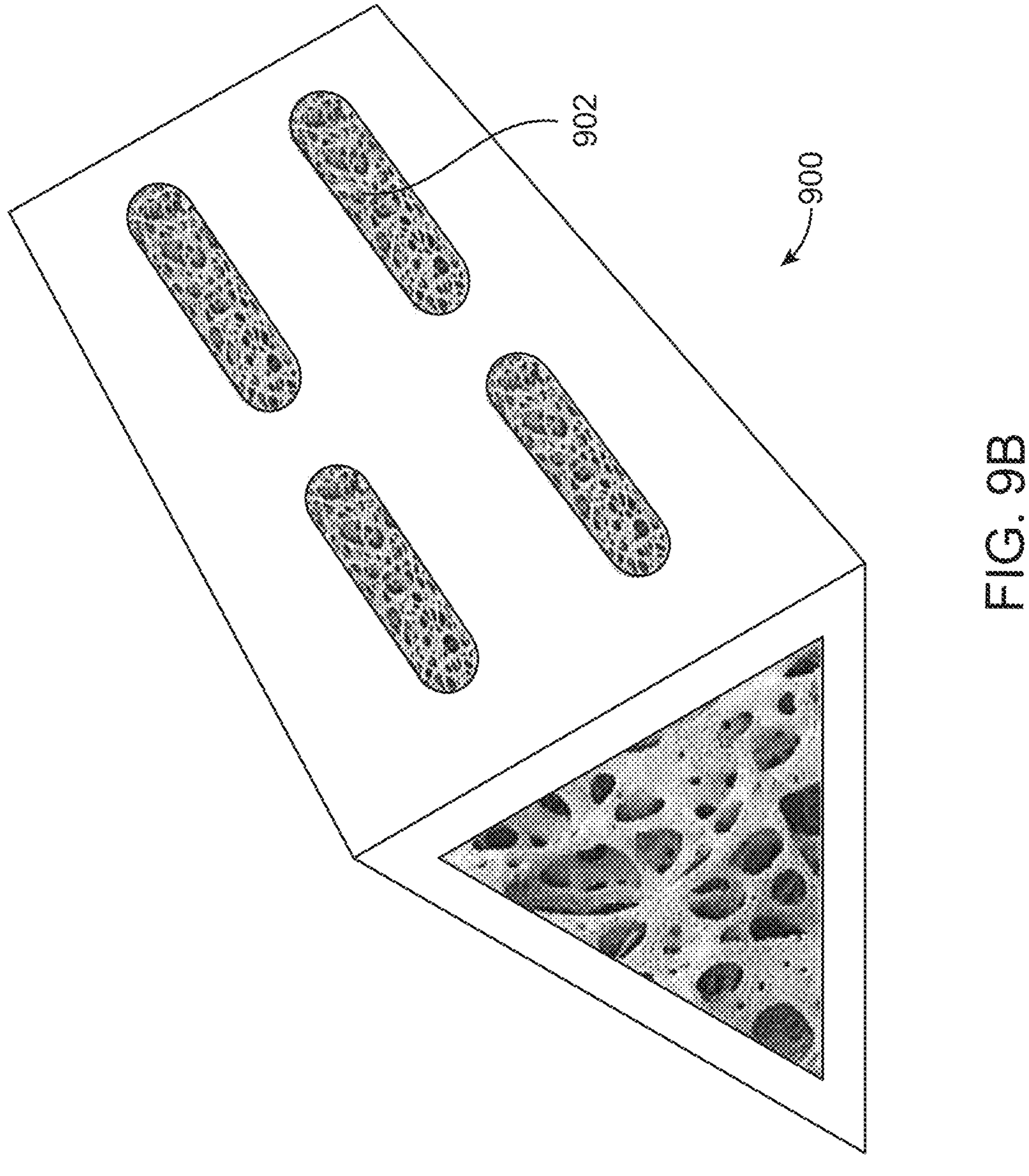

In some embodiments, as illustrated in FIGS. 8A and 8B, the distal portion of the plurality of walls 802 forming the implant structure 800 can have fenestrations 806. For example, the distal portion of the implant structure 800 that is configured to be embedded in the sacrum or second bone segment can be fenestrated, while the proximal portion of the implant structure 800 that is configured to be embedded in the illium or first bone segment can be free from fenestrations. In other embodiments, the proximal portion of the implant structure 800 can be fenestrated while the distal portion of the implant structure 800 can be free from fenestration. In other embodiments, as illustrated in FIGS. 9A and 9B and the other embodiments described herein, the fenestrations can be distributed across the entire face of each wall or side of the implant structure. In some embodiments, the concentration or number of fenestrations can be higher in one portion of the implant structure than the other.

In some embodiments, as illustrated in FIGS. 8A and 8B, the fenestrations 806 can be oval or circular shaped or curvilinear, such that the fenestrations 806 do not have corners. In some embodiments, the fenestrations 806 can be staggered, arranged randomly, or otherwise distributed in a non-aligned pattern across each wall 802. For example, in some embodiments, each longitudinal row of fenestrations can be staggered or offset from adjacent longitudinal rows of fenestrations. In some embodiments, the fenestrations can alternatively or additionally be staggered along the longitudinal axis of the implant structure 800. This non-aligned arrangement of fenestrations can provide the implant structure with improved structural strength.

In some embodiments, the implant structure 800 can be sized as any other implant structure described herein. In some embodiments, the implant structure 800 can be sized so that the implant structure 800 has walls that inscribe a circle with a diameter of about 8 mm, or between about 4 and 12 mm, as illustrated in FIG. 8B. In some embodiments, the implant structure 800 can be sized so that the wall inscribe a circle with a diameter equal to or about equal to the diameter of a guide pin. In some embodiments, the implant structure 800 can have a proximal end 808 having a cap 810 with a circular opening 812 that allows passage of a guide pin.

In some embodiments, as illustrated in FIGS. 9A and 9B, the implant structure 900 can be similar to the embodiment described in FIGS. 8A and 8B except that the fenestrations 902 are evenly distributed across the faces of the implant structure. FIG. 9B illustrates bone growing within and/or through the fenestrations 902 and lumen of the implant structure 900. In some embodiments, the bone illustrated within the lumen of the implant structure 900 may be native bone that remains after the implant structure 900 is advanced into the bone, i.e. a self-grafting implant. In some embodiments, the lumen of the implant structure 900 illustrated in FIGS. 9A and 9B, as well as the other implant structures described herein, can be filled with bone material and/or a biologic aid such as morselized bone, allograft bone, autograft bone, hydroxyapatite, bone morphogenetic protein and the like to promote bony ingrowth within the implant structure 900. This can be appropriate when the implant structure 900 is inserted into a bore such that after implantation, the lumen of the implant structure 900 is empty or substantially empty and can be filled with bone growth promoting materials. In addition, as described above, the interior surface and/or the outer surface of the implant structure can be roughened and/or coated, using a plasma coating process for example, to provide a porous or roughened surface.

The terms "about" and "approximately" and the like can mean within 10, 20, or 30% of the stated value or range.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiments whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An implant for bone fixation, comprising:

an elongate body having a longitudinal axis and a rectilinear cross section transverse to the longitudinal axis, a first face, a second face, and a third face, each extending longitudinally along the elongate body, wherein each of the first face, second face, and third face form an apex with an adjacent face, wherein the second face extends between an apex with the first face and an apex with the third face, wherein a distal portion of the elongate body that is configured to be implanted in a sacrum includes a plurality of fenestrations on each face, and a proximal portion of the elongate body that is proximal relative to the distal portion of the elongate body and that is configured to be implanted in an ilium is free from fenestrations, wherein the implant has a bending strength or a shear strength of 0.5 to 0.9 relative to a reference implant that is cannulated but otherwise solid and which has a bending strength of 1.00 and a shear strength of 1.00.

2. The implant of claim 1, wherein each apex is chamfered at its distal end to provide three sloping distal shoulders.

3. The implant of claim 1, wherein the plurality of fenestrations on each face are arranged in a staggered pattern.

4. The implant of claim 3, wherein the plurality of fenestrations on each face comprises a plurality of rows of fenestrations, and wherein on each face the fenestrations in a first row are staggered from the fenestrations in a second row.

5. The implant of claim 1, wherein the elongate body has a triangular cross section transverse to the longitudinal axis.

6. The implant of claim 1, wherein the plurality of fenestrations have circular shapes.

7. The implant of claim 1, wherein the plurality of fenestrations have oval shapes.

8. The implant of claim 1, further comprising a fourth face extending between an apex with the first face and an apex with the third face.

* * * * *